(12) United States Patent
Minomi et al.

(10) Patent No.: US 11,298,371 B2
(45) Date of Patent: Apr. 12, 2022

(54) REGULATION OF NUCLEIC ACID MOLECULE EXPRESSION

(71) Applicant: NITTO DENKO CORPORATION, Ibaraki (JP)

(72) Inventors: Kenjiro Minomi, Ibaraki (JP); Naoko Urushihara, Ibaraki (JP); Yusuke Nakashima, Ibaraki (JP); Hiroyuki Tanaka, Ibaraki (JP); Erika Terada, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 16/754,595

(22) PCT Filed: Oct. 11, 2018

(86) PCT No.: PCT/JP2018/037975
§ 371 (c)(1),
(2) Date: Apr. 8, 2020

(87) PCT Pub. No.: WO2018/074071
PCT Pub. Date: Apr. 18, 2019

(65) Prior Publication Data
US 2020/0261491 A1 Aug. 20, 2020

(30) Foreign Application Priority Data
Oct. 11, 2017 (JP) .............................. JP2017-197990

(51) Int. Cl.
C07H 21/02 (2006.01)
A61K 31/713 (2006.01)
C12N 15/113 (2010.01)

(52) U.S. Cl.
CPC .......... *A61K 31/713* (2013.01); *C12N 15/113* (2013.01)

(58) Field of Classification Search
CPC .................................................. C12N 15/113
See application file for complete search history.

(56) References Cited

U.S. PATENT DOCUMENTS

| | | |
|---|---|---|
| 5,871,921 A | 2/1999 | Landegren et al. |
| 2002/0048761 A1 | 4/2002 | Lizardi |
| 2007/0122827 A1 | 5/2007 | Sorge et al. |
| 2009/0208564 A1 | 8/2009 | Li et al. |
| 2010/0015617 A1 | 1/2010 | Toyama |
| 2010/0173974 A1 | 7/2010 | Brown |
| 2010/0184841 A1 | 7/2010 | Brown |
| 2012/0010271 A1 | 1/2012 | Ohgi et al. |

FOREIGN PATENT DOCUMENTS

| | | |
|---|---|---|
| JP | H9-509063 A | 9/1997 |
| JP | 2002-525049 A | 8/2002 |
| JP | 2008-099673 A | 5/2008 |
| JP | 2009-511055 A | 3/2009 |
| WO | WO 2000/015779 A2 | 3/2000 |
| WO | WO 2007/044864 A2 | 4/2007 |
| WO | WO 2009/029688 A1 | 3/2009 |
| WO | WO 2010/080129 A1 | 7/2010 |
| WO | WO 2011/103394 A1 | 8/2011 |
| WO | WO 2012/005368 A1 | 1/2012 |

OTHER PUBLICATIONS

Lubeck et al. (Nucleic Acids Research, vol. 31, No. 15, 2003, 4417-4424).*
Vazquez-Anderson et al. (Nucleic Acids Research, vol. 45, No. 9, 2017, 5523-5538).*
Elbashir et al., "Duplexes of 21-nucleotide RNAs mediate RNA interference in cultured mammalian cells", Nature. 2001;411 (6836):494-8.
Stephenson et al., "Inhibition of Rous sarcoma viral RNA translation by a specific oligodeoxyribonucleotide", Proc Natl Acad Sci U S A. 1978;75(1):285-8.
Yamakawa, et al., "Properties of Nicked and Circular Dumbbell RNA/DNA Chimeric Oligonucleotides A Containing Anti sense Phosphodiester Oligodeoxynucleotides", Bioorganic & Medicinal Chemistry, 1998, vol. 6, pp. 1025-1032.
Yoshimura et al., "Inhibition of intimal hyperplasia after balloon injury in rat carotid artery model using cis-element 'decoy' of nuclear factor-kB binding site as a novel molecular strategy", Gene Ther. 2001;8(21):1635-42.
Zamecnik et el., "Inhibition of Rous sarcoma virus replication and cell transformation by a specific oligodeoxynucleotide", Proc Natl Acad Sci U S A. 1978;75(1):280-4.
International Search Report issued in patent application No. PCT/JP2018/037975, dated Dec. 25, 2018.
Lee, Jong Bum et al., "Self-assembled RNA interference microsponges for efficient siRNA delivery" Nature Materials, Nature Publishing Group, London, GB, 2012, vol. 11, No. 4, pp. 316-322.
Extended European Search Report in Application No. 18866443.7, dated Jun. 9, 2021.
Zhang et al., "Circular siRNAs for Reducing Off-Target Effects and Enhancing Long-Term Gene Silencing in Cells and Mice" Molecular Therapy: Nucleic Acids, Mar. 2018, vol. 10, pp. 237-244.

\* cited by examiner

*Primary Examiner* — Amy H Bowman
(74) *Attorney, Agent, or Firm* — Knobbe Martens Olson & Bear, LLP

(57) ABSTRACT

The present invention provides a nucleic acid molecule dimer that includes a first nucleic acid molecule having complementarity with at least part of a target nucleic acid molecule, and a second nucleic acid molecule having complementarity with the first nucleic acid molecule, wherein the first nucleic acid molecule has a linear form, the second nucleic acid molecule has a cyclic form, and the first and second nucleic acid molecules at least partially form a double strand.

16 Claims, 7 Drawing Sheets
Specification includes a Sequence Listing.

REGULATION OF NUCLEIC ACID MOLECULE EXPRESSION

BACKGROUND

Reference to Sequence Listing

A Sequence Listing submitted as an ASCII text file via EFS-Web is hereby incorporated by reference in accordance with 35 U.S.C. § 1.52(e). The name of the ASCII text file for the Sequence Listing is 2020-04-02 Sequence Listing—ABE001.001APC, the date of creation of the ASCII text file is Apr. 2, 2020, and the size of the ASCII text file is 9.73 KB.

TECHNICAL FIELD

The present disclosure relates to a nucleic acid molecule that modulates the expression of a target nucleic acid molecule, a composition comprising the nucleic acid molecule, a method for modulating the expression of a target nucleic acid molecule using the nucleic acid molecule, etc.

BACKGROUND ART

Since Zamecnik and Stephenson reported the sequence-specific suppression of gene expression with an oligonucleic acid (antisense method) (Non-Patent Literatures 1 and 2), nucleic acid drugs that control gene expression have been developed using nucleic acid molecules. The nucleic acid drugs include antisense nucleic acids for use in the antisense method as well as nucleic acid molecules having various structures for use in RNA interference (Non-Patent Literature 3 and Patent Literatures 1 to 4), decoy nucleic acids targeting transcriptional factors (Non-Patent Literature 4), etc.

CITATION LIST

Patent Literature

Patent Literature 1: WO 2009/029688
Patent Literature 1: WO 2010/080129
Patent Literature 1: WO 2011/103394
Patent Literature 1: WO 2012/005368

Non-Patent Literature

Non-Patent Literature 1: Zamecnik and Stephenson, Proc Natl Acad Sci USA. 1978; 75(1):280-4
Non-Patent Literature 2: Stephenson and Zamecnik, Proc Natl Acad Sci USA. 1978; 75(1):285-8
Non-Patent Literature 3: Elbashir et al., Nature. 2001; 411 (6836):494-8
Non-Patent Literature 4: Yoshimura et al., Gene Ther. 2001; 8(21):1635-42

SUMMARY

Problems to be Solved by the Invention

There has been a demand for the development of nucleic acid drugs having advantages such as less off-target effects, high chemical stability, and easy design or production.

Solution to Problem

Some aspects of the present disclosure relate to the following.

[1] A nucleic acid molecule dimer comprising: a first nucleic acid molecule having complementarity to at least a portion of a target nucleic acid molecule; and a second nucleic acid molecule having complementarity to the first nucleic acid molecule, wherein the first nucleic acid molecule is linear, the second nucleic acid molecule is circular, and the first nucleic acid molecule and the second nucleic acid molecule at least partially form a duplex.
[2] The nucleic acid molecule dimer according to [1], wherein the first nucleic acid molecule is longer than the second nucleic acid molecule.
[3] The nucleic acid molecule dimer according to [1] or [2], wherein the 3' end or the 5' end of the first nucleic acid molecule forms a overhang.
[4] The nucleic acid molecule dimer according to any one of [1] to [3], wherein the first nucleic acid molecule forms a nick.
[5] The nucleic acid molecule dimer according to any one of [1] to [4], wherein the length of the first nucleic acid molecule is 16 to 30 mer.
[6] The nucleic acid molecule dimer according to any one of [1] to [5], wherein the length of the second nucleic acid molecule is 9 to 30 mer.
[7] The nucleic acid molecule dimer according to any one of [1] to [6], wherein the first nucleic acid molecule and/or the second nucleic acid molecule is modified.
[8] A composition comprising a nucleic acid molecule dimer according to any one of [1] to [7].
[9] A pharmaceutical composition comprising a nucleic acid molecule dimer according to any one of [1] to [7] and one or more pharmaceutically acceptable additives.
[10] The nucleic acid molecule dimer according to any one of [1] to [7] or the composition according to [8] or [9] for use in the modulation of expression of a target nucleic acid molecule.
[11] The nucleic acid molecule dimer according to any one of [1] to [7] or the composition according to [8] or [9] for use in the treatment of a disease associated with a target nucleic acid molecule.
[12] A method for treating a disease associated with a target nucleic acid molecule, comprising administering an effective amount of a nucleic acid molecule dimer according to any one of [1] to [7] or a composition according to [8] or [9] to a subject in need thereof.

Advantageous Effects of Invention

The nucleic acid molecule according to the present disclosure exerts one or two or more of the following effects.
(1) The nucleic acid molecule can modulate the expression of a targeted nucleic acid molecule.
(2) The nucleic acid molecule produces less off-target effects ascribable to a target-non-complementary nucleic acid molecule.
(3) The nucleic acid molecule can circumvent the induction of sequence-non-specific cell response by a nucleic acid molecule.
(4) The nucleic acid molecule can circumvent the induction of phosphorylation of PKR.
(5) The nucleic acid molecule can circumvent the activation of the TLR pathway.
(6) The nucleic acid molecule is highly stable in blood.
(7) The nucleic acid molecule is highly resistant to nuclease.
(8) The nucleic acid molecule is easy to design.
(9) The nucleic acid molecule is easy to produce.

DETAILED DESCRIPTION

Figure 1:
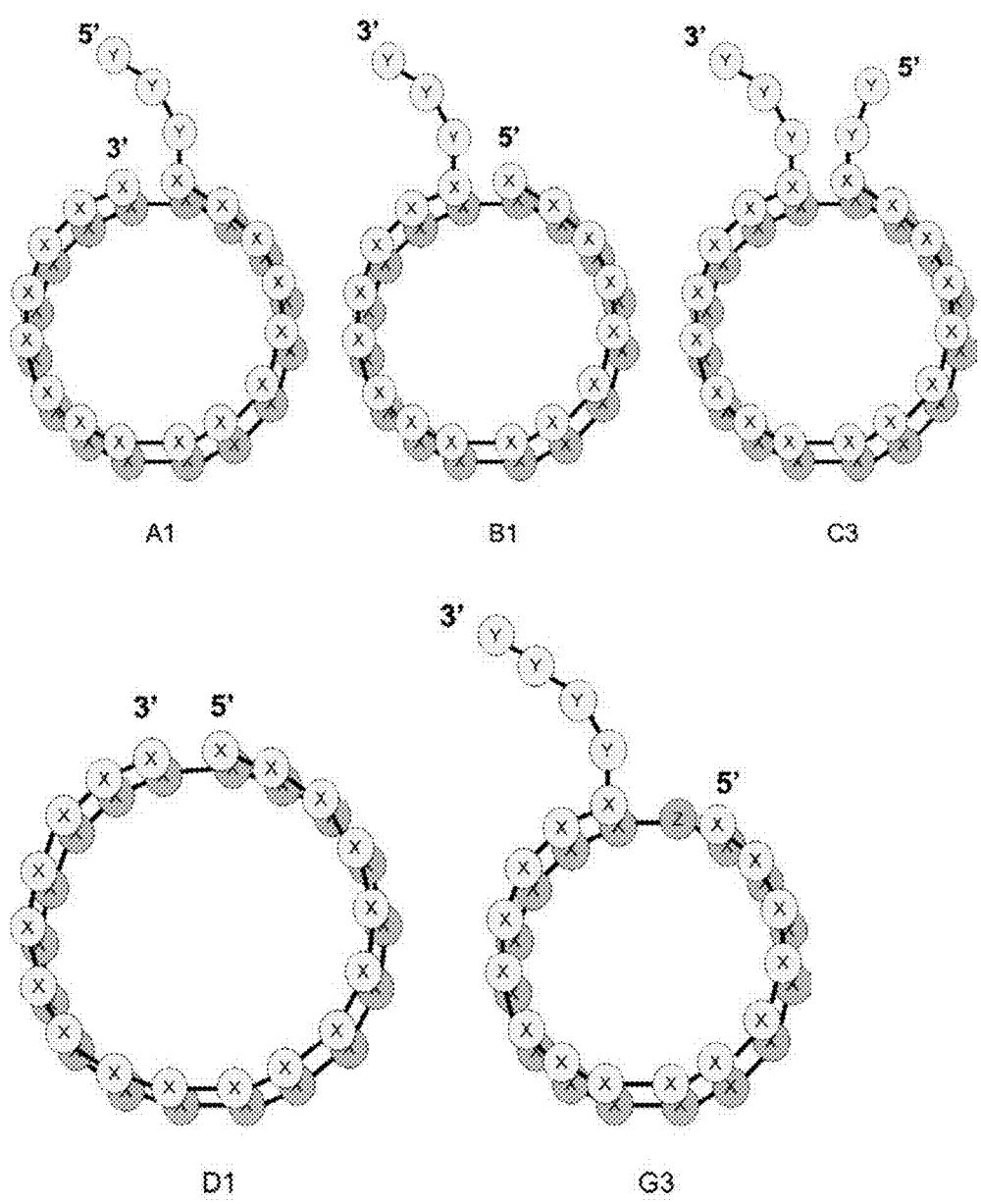
FIG. 1 is a diagram showing schematic views of some forms of the nucleic acid molecule dimer of the present disclosure. Upper white constructs having a 5' end and a 3' end depict TCNA. Lower gray constructs having neither a 5' end nor a 3' end depict TNNA. Particles represented by X, Y or Z depict nucleotides. Lines linking the particles depict internucleotide bonds.

All technical terms and scientific terms used herein have the same meanings as those usually understood by those skilled in the art, unless otherwise specified herein. All patents, applications and other publications (including online information) cited herein are incorporated herein by reference in their entirety.

The present specification encompasses the contents described in the specification and drawings of the Japanese application filed on Oct. 11, 2017 (Japanese Application No. 2017-197990), based on which the priority of the present applications is claimed.

In one aspect, the present disclosure relates to a nucleic acid molecule dimer (hereinafter, also referred to as the "nucleic acid molecule of the present disclosure", the "circular TNNA-containing nucleic acid molecule dimer", etc.) comprising: a first nucleic acid molecule having complementarity to at least a portion of a target nucleic acid molecule (also referred to as a target-complementary nucleic acid: TCNA); and a second nucleic acid molecule having complementarity to the first nucleic acid molecule (also referred to as a target-non-complementary nucleic acid: TNNA), wherein the first nucleic acid molecule is linear, the second nucleic acid molecule is circular, and the first nucleic acid molecule and the second nucleic acid molecule at least partially form a duplex.

In the present disclosure, the "target nucleic acid molecule" means a nucleic acid molecule whose expression is to be modulated by the nucleic acid molecule of the present disclosure. Examples of the target nucleic acid molecule include, but are not limited to, RNA and DNA present in cells. The target nucleic acid molecule may be endogenous or exogenous. Examples of the RNA include, but are not limited to, messenger RNA (mRNA), pre-mRNA, microRNA (miRNA), pre-miRNA, PIWI-interacting RNA (piRNA), long non-coding RNA (lncRNA), nuclear non-coding RNA, mitochondrial non-coding RNA, RNA transcripts such as antisense transcripts, and viral RNA. Examples of the DNA include nuclear DNA, mitochondrial DNA, and viral DNA. The target nucleic acid molecule may encode an expression product such as a protein (e.g., mRNA and viral RNA) or may not encode such an expression product (e.g., miRNA, piRNA, various types of non-coding RNA, and antisense transcripts). Also, the target nucleic acid molecule may have biological activity in itself (e.g., miRNA and piRNA). In some embodiments, the expression product encoded by the target nucleic acid molecule is related to a disease. In some embodiments, the target nucleic acid molecule is subject to RNA silencing. Examples of the target nucleic acid molecule that is subject to RNA silencing include, but are not limited to, RNA transcripts present in cytoplasms or nuclei, and viral RNA. In other embodiments, the target nucleic acid molecule is subject to RNA activation (RNAa). Examples of the target nucleic acid molecule that is subject to RNA activation include, but are not limited to, DNA such as nuclear DNA and mitochondrial DNA, and RNA such as non-coding RNA located near DNA.

The RNA silencing typically refers to a gene expression control mechanism by small RNA and includes RNA interference (RNAi), a gene expression control mechanism by miRNA, and a gene expression control mechanism by piRNA.

The RNA interference typically refers to a phenomenon, induced by a double-stranded nucleic acid molecule, in which target RNA is degraded in a sequence-specific manner. Upon entrance into a cell, the double-stranded nucleic acid molecule is cleaved by dicer according to its length and then incorporated into RNA-induced silencing complex (RISC) containing Argonaute (AGO) protein. RISC is guided by an antisense strand (guide strand) having a sequence complementary to target RNA so that the RISC recognizes and cleaves the target RNA. When the target RNA is mRNA, a protein, etc. encoded by the mRNA is no longer expressed (gene silencing). When the target RNA is miRNA or an antisense transcript, the effect of the miRNA or the antisense transcript disappears. If the miRNA or the antisense transcript acts to suppress gene expression, the expression of the gene may be increased through the degradation of the miRNA or the antisense transcript by the RNA interference.

The gene expression control mechanism by miRNA typically refers to sequence-specific degradation or translational suppression of RNA induced by miRNA. Mature miRNA is incorporated into miRNA-induced silencing complex (miRISC) containing Argonaute (AGO) protein so that the mature miRNA mainly suppresses translation from mRNA by inducing the miRISC to the mRNA complementary to a seed sequence (sequence from positions 2 to 8 from the 5' end), and also promotes the degradation of the mRNA by degrading the 3'-terminal poly-A tail of the mRNA for truncation.

The gene expression control mechanism by piRNA typically refers to sequence-specific degradation of RNA induced by piRNA. piRNA is incorporated into piRNA-induced silencing complex (piRISC) containing Piwi protein, a protein of the PIWI subfamily, and then translocated into the nucleus to suppress the transcription of the target gene in a sequence-specific manner.

The RNA activation typically refers to a phenomenon in which the expression of a gene is increased by double-stranded RNA targeting a promoter region of the gene (Li et al., Proc Natl Acad Sci USA. 2006; 103 (46): 17337-42). The targeted nucleic acid molecule may be DNA (Li, supra) or may be a transcript that overlaps with the promoter region (e.g., a non-coding transcript) (Jiao and Slack, Epigenetics. 2014; 9 (1): 27-36). The RNA activation has been confirmed so far in a plurality of genes such as E-cadherin, p21, VEGF, progesterone receptor (PR), p53, and Nanog genes (Jiao and Slack, supra). Small RNA that brings about the RNA activation is also called small activating RNA (saRNA).

In the present disclosure, the term "having complementarity" or "being complementary" means that a nucleic acid molecule (first nucleic acid molecule) can form a hydrogen bond with another nucleic acid molecule (second nucleic acid molecule) through Watson-Crick base pairing, non-Watson-Crick base pairing, or the like. The degree of complementarity can vary. The degree of complementarity can be indicated by, for example, the percentage of consecutive nucleic acid residues of the first nucleic acid molecule that can form a hydrogen bond (e.g., a Watson-Crick base pair) with nucleic acid residues of the second nucleic acid molecule (complementarity percent). For example, the first nucleic acid molecule and the second nucleic acid molecule may each be constituted by a total of 10 nucleotides, and 5, 6, 7, 8, 9 or 10 out of the 10 nucleotides constituting the first nucleic acid molecule form a base pair with the second nucleic acid molecule having 10 nucleotides. In such a case, the complementarity percent is 50%, 60%, 70%, 80%, 90% or 100%, respectively. The term "having complete complementarity" or "being completely complementary" means that all the consecutive nucleic acid residues of the first nucleic acid molecule form a hydrogen bond with the same number there as of consecutive nucleic acid residues in the second nucleic acid molecule. In one embodiment, the first nucleic acid molecule in the nucleic acid molecule dimer of the present disclosure comprises approximately 15 to approximately 30 or more (e.g., approximately 15, 16, 17, 18, 19, 20, 21, 22, 23, 24, 25, 26, 27, 28, 29, 30 or more) nucleotides complementary to one or two or more target nucleic acid molecules or portion(s) thereof.

The TCNA in the nucleic acid molecule of the present disclosure is one of the nucleic acid molecules constituting this nucleic acid molecule dimer (also referred to as a double-stranded nucleic acid molecule) and has complementarity to at least a portion of a target nucleic acid molecule. The degree of complementarity can be any degree to which the TCNA can recognize the target nucleic acid molecule in RNA silencing, RNA activation, or the like, and is not necessarily required to be 100% complementarity. Thus, the TCNA may have a mismatch with a target sequence in the target nucleic acid molecule. The number of mismatches may be 1, 2, 3, 4, 5 or 6 or more, though differing depending on the binding free energy between the TCNA and the target site of the target nucleic acid molecule. The mismatch may be established at any position of the TCNA and is preferably established at the 5' end from the viewpoint of RNA silencing efficiency, etc. In some embodiments, the TCNA has 100% complementarity (i.e., the number of mismatches is zero) to the target sequence. In other embodiments, the TCNA has complementarity of at least approximately 80%, at least approximately 85%, at least approximately 90%, at least approximately 91%, at least approximately 92%, at least approximately 93%, at least approximately 94%, at least approximately 95%, at least approximately 96%, at least approximately 97%, at least approximately 98%, or at least approximately 99%, etc. to the target sequence. In a particular embodiment, the TCNA contains 1, 2, 3, 4, 5 or 6 or more mismatches to the target sequence.

When the TCNA controls the expression of the target nucleic acid molecule through the gene expression control mechanism by miRNA or a gene expression control mechanism similar thereto, the complementarity of the TCNA to the target nucleic acid molecule may be based on the complementarity of the miRNA to its target nucleic acid molecule. In the TCNA, for example, a portion corresponding to at least a seed region of the miRNA may be complementary to the target nucleic acid molecule. Specifically, such TCNA includes a form in which only the portion corresponding to at least a seed region of the miRNA is complementary to the target nucleic acid molecule. The portion of the TCNA corresponding to the seed region of the miRNA may have 100% complementarity to the target nucleic acid molecule, or may have, for example, 1, 2, 3, 4 or 5, preferably 1 mismatch. The TCNA that controls the expression of the target nucleic acid molecule through the gene expression control mechanism by miRNA or a gene expression control mechanism similar thereto may have, for example, the nucleotide sequence of the miRNA comprising the seed region (e.g., mature miRNA). The target nucleic acid molecule of the nucleic acid molecule of the present disclosure comprising such TCNA may be similar to the target nucleic acid molecule of the miRNA. In general, miRNA is known to target a plurality of different nucleic acid molecules. Thus, the nucleic acid molecule of the present disclosure comprising the TCNA that controls the expression of the target nucleic acid molecule through the gene expression control mechanism by miRNA or a gene expression control mechanism similar thereto can control the expression of a plurality of target nucleic acid molecules.

The length of the TCNA is not particularly limited as long as the nucleic acid molecule dimer of the present disclosure can achieve one or two or more of the effects such as RNA silencing and RNA activation. The length may be approximately 1 to approximately 49 mer, more preferably approximately 15 to approximately 30 mer. In this context, the term "mer" represents the number of monomers (e.g., nucleotides) constituting TCNA or TNNA. In some embodiments, the TCNA has a length suitable for incorporation into RISC (e.g., approximately 15 mer to approximately 25 mer). In other embodiments, the TCNA has a length suitable as a dicer substrate (e.g., approximately 25 to approximately 30 mer). In a particular embodiment, the TCNA has a length of 15, 16, 17, 18, 19, 20, 21, 22, 23, 24, 25, 26, 27, 28, 29 or 30 mer.

The TCNA may have a sequence feature suitable for the induction of RNA interference. Examples of such a sequence feature include (1) A or U at position 1, (2) G or C at position 19, (3) 4 to 7 bases of A or U at positions 1 to 7, (4) less than 10 consecutive bases of G or C, (5) a GC content of 30% to 52%, (6) 3 or more bases of A or U at positions 1 to 5, (7) the absence of an internal repeat sequence, (8) A at position 1, (9) A at position 17, (10) U at position 10, (11) a base other than G at position 7, (12) A or U at position 14, (13) a base other than U at position 19, (14) a base other than G or C at position 1, (15) a base other than G at position 1, and combinations thereof. For the suppression of off-target effects, a sequence from positions 2 to 8 of the TCNA may be designed such that the melting temperature (Tm) thereof is low (e.g., approximately 30° C. or lower, preferably approximately 25° C. or lower, more preferably approximately 21.5° C. or lower), when the polynucleotide from positions 2 to 8 forms a duplex with a polynucleotide having a complementary sequence. The melting temperature can be lowered, for example, by decreasing the number of G/C base pairs.

Particular non-limiting examples of the TCNA include those having the nucleotide sequences represented by SEQ ID NOs: 25 to 31 and 33 to 35 described in Table 2.

Other particular non-limiting examples of the TCNA include those having the nucleotide sequences represented by SEQ ID NO: 38 described in Table 12 and SEQ ID NOs: 42 and 43 described in Table 16.

Further particular non-limiting examples of the TCNA include those having the nucleotide sequence of miRNA (preferably mature miRNA) comprising a seed region.

In the present specification, positions on a nucleotide sequence are described in order from the 5' end toward the 3' end unless otherwise specified.

The TNNA in the nucleic acid molecule dimer of the present disclosure is one of the strands constituting this nucleic acid molecule dimer and has complementarity to TCNA. The degree of complementarity can be any degree to which the nucleic acid molecule dimer can exert one or two or more of the effects such as RNA silencing and RNA activation, and is not necessarily required to be 100% complementarity. Thus, the TNNA may have a mismatch with TCNA. The number of mismatches may be 1, 2, 3, 4, 5 or 6 or more, though differing depending on the binding free energy between the TNNA and TCNA. The mismatch may be established at any position of the TNNA. In some embodiments, the TNNA has 100% complementarity (i.e., the number of mismatches is zero) to TCNA. In other embodiments, the TNNA has complementarity of at least approximately 80%, at least approximately 85%, at least approximately 90%, at least approximately 91%, at least approximately 92%, at least approximately 93%, at least approximately 94%, at least approximately 95%, at least approximately 96%, at least approximately 97%, at least approximately 98%, or at least approximately 99%, etc. to TCNA. In a particular embodiment, the TCNA contains 1, 2, 3, 4, 5 or 6 or more mismatches to TCNA.

The length of the TNNA is not particularly limited as long as the nucleic acid molecule dimer of the present disclosure can achieve one or two or more of the effects such as RNA silencing and RNA activation. The length may be approximately 2 to approximately 49 mer, more preferably approximately 9 to approximately 30 mer. In some embodiments, the TNNA has a length suitable for the incorporation of TCNA into RISC (e.g., approximately 15 to approximately 25 mer). In other embodiments, the TNNA has a length suitable as a dicer substrate (e.g., approximately 25 to approximately 30 mer). In a particular embodiment, the TNNA has a length of 9, 10, 11, 12, 13, 14, 15, 16, 17, 18, 19, 20, 21, 22, 23, 24, 25, 26, 27, 28, 29 or 30 mer. The length of the TNNA equal to or smaller than 16 mer can suppress off-target effects ascribable to the TNNA even when the circular TNNA is cleaved with nuclease or the like so that the nucleic acid molecule dimer of the present disclosure is linearized.

The nucleotide sequence of the TNNA depends largely on the nucleotide sequence of TCNA because the TNNA forms a duplex with the TCNA. In order to form a circular structure, the TNNA may have a sequence feature as described below. For example, the nucleotide sequence of the TNNA can be designed so as not to form repeats of a simple sequence, continuation of the same bases, a palindromic structure, or the like, which brings about the endocyclic formation of a duplex when the TNNA is circularized. The number of repeats of a simple sequence can be, for example, 3 or less, preferably 2 or less. The number of continuation of the same bases can be, for example, 5 or less, preferably 4 or less. The number of bases capable of endocyclically forming a pair can be approximately 80% or less, preferably approximately 75% or less, more preferably approximately 70% or less, of the total number of bases of the TNNA. The number of bases capable of endocyclically forming a G/C pair can be approximately 40% or less, preferably approximately 35% or less, more preferably approximately 30% or less, further preferably approximately 25% or less, of the total number of bases of the TNNA. The number of bases capable of endocyclically forming the longest consecutive pairs can be approximately 60% or less, preferably approximately 55% or less, more preferably approximately 50% or less, further preferably approximately 45% or less, of the total number of bases of the TNNA. The number of bases capable of endocyclically forming a pair can be determined, for example, by counting the number of facing bases complementary to each other when the nucleotide sequence of the TNNA is folded at its center.

For example, when the sequence of TNNA having 16 bases is represented by

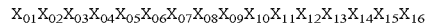

wherein $X_n$ represents a nucleotide, and n represents a nucleotide number,
this sequence is folded at its center (between $X_{08}$ and $X_{09}$) to form

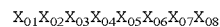
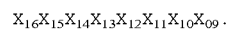

In this context, for example, when four pairs of $X_{02}$ and $X_{15}$, $X_{04}$ and $X_{13}$, $X_{05}$ and $X_{12}$, and $X_{06}$ and $X_{11}$ are complementary to each other, the number of bases capable of endocyclically forming a pair is 8 which constitutes 50% of the total number of bases of the TNNA. Also, the number of bases capable of endocyclically the longest consecutive pairs is 6 ($X_{04}$ with $X_{13}$, $X_{05}$ with $X_{12}$, and $X_{06}$ with $X_{11}$) which constitutes 37.5% of the total number of bases.

The circular TNNA has neither particular 5' nor 3' end. Therefore, the largest value of each numerical value such as the number of bases capable of endocyclically forming a pair can be determined by determining the number of bases capable of forming a pair in the same way as above as to all possible folding positions while the folding position is shifted by one base. For example, the folding position in the sequence described above is shifted by one base to form $$X_{02}X_{03}X_{04}X_{05}X_{06}X_{07}X_{08}X_{09}$$
$$X_{01}X_{16}X_{15}X_{14}X_{13}X_{12}X_{11}X_{10}$$
or
$$X_{16}X_{01}X_{02}X_{03}X_{04}X_{05}X_{06}X_{07}$$
$$X_{15}X_{14}X_{13}X_{12}X_{11}X_{10}X_{09}X_{08}.$$

In this state, the number of bases capable of forming a pair is determined.

As for TNNA having an odd number of bases, for example, TNNA having 17 bases is taken as an example. This sequence is folded into $$X_{01}X_{02}X_{03}X_{04}X_{05}X_{06}X_{07}X_{08}X_{09}$$
$$X_{17}X_{16}X_{15}X_{14}X_{13}X_{12}X_{11}X_{10}$$
or
$$X_{01}X_{02}X_{03}X_{04}X_{05}X_{06}X_{07}X_{08}$$
$$X_{17}X_{16}X_{15}X_{14}X_{13}X_{12}X_{11}X_{10}X_{09}.$$

Counting can be performed in the same way as in the even number of bases.

Particular non-limiting examples of the TNNA include those having the nucleotide sequences represented by SEQ ID NOs: 1 to 11 described in Table 1.

Other particular non-limiting examples of the TNNA include those having the nucleotide sequences represented by SEQ ID NO: 37 described in Table 12 and SEQ ID NO: 41 described in Table 15.

Further particular non-limiting examples of the TNNA include those having a nucleotide sequence complementary to the nucleotide sequence of miRNA (preferably mature miRNA) comprising a seed region.

In the nucleic acid molecule dimer of the present disclosure, the TCNA is linear. The term "being linear" means that the TCNA has a modified or unmodified 5' end and 3' end, and these ends are not attached through a covalent bond. In the nucleic acid molecule dimer of the present disclosure, the TNNA is circular. The term "being circular" means that all monomers, such as nucleotides, constituting the TNNA are attached to each other without having both the 5' end and the 3' end and without forming a duplex region within the circular TNNA. In actuality, the circular TNNA has neither a 5' end nor a 3' end. However, locations where the 5' end and the 3' end are formed by the cleavage of the bond between monomers at a particular position (e.g., locations of the 5' end and the 3' end of uncircularized linear TNNA when the circular TNNA is obtained by the circularization of the linear TNNA) are also referred to as the 5' end and the 3' end of the circular TNNA for the sake of convenience.

When the circular TNNA is obtained by the circularization of linear TNNA, the monomers located at the 5' end and the 3' end in the linear TNNA are typically attached through a phosphodiester bond and may be attached through another manner. Examples of another attachment manner include phosphorothioate, 3'- (or -5') deoxy-3'- (or -5') thio-phosphorothioate, phosphorodithioate, phosphoroselenate, 3'- (or -5') deoxyphosphinate, boranophosphate, 3'- (or -5') deoxy-3'- (or 5'-) aminophosphoramidate, hydrogen phosphonate, boranophosphoric acid ester, phosphoramidate, alkyl or aryl phosphonate, phosphotriester, phosphorus bonds, amide bonds, morpholino, modified internucleotide bonds such as 2'-5' bonds, disulfide bonds, and bonds via spacers.

In the case of attaching the 5' end and the 3' end of linear circular TNNA via a spacer, it is preferred to design such a molecule such that the spacer of the TNNA is located at the same position as that of a spacer introduced in TCNA or located at a position that does not overlap with TCNA, when the circularized TNNA is annealed to the TCNA. The position that does not overlap with TCNA is, for example, between the 5' end and the 3' end of the TCNA when the TCNA has no overhang, between the 3' end and the base of a 5' overhang of the TCNA when the TCNA has the 5' overhang, between the 5' end and the base of a 3' overhang of the TCNA when the TCNA has the 3' overhang, or between the bases of two overhangs of the TCNA when the TCNA has both terminal overhangs. Examples of the spacer include abasic nucleotides, polyether (e.g., polyethylene glycol), polyamine, polyamide, peptides, and glycerin.

The position of the bond between both terminal monomers of the linear TNNA is not particularly limited and can be set to an arbitrary position of circularized TNNA. In order to discriminate this bond from bonds between other monomers constituting the circular TNNA, the bond is also referred to as an "interterminal bond". The position of the interterminal bond can be adjusted by, for example, the sequence design of the linear TNNA. The interterminal bond may be the same as or different from bonds between other monomers in the circular TNNA.

Whether the TNNA is circular can be confirmed, for example, by the conformational analysis of the TNNA by NMR, AFM, or the like, the evaluation of resistance to exonuclease (comparison with a linear nucleic acid molecule), the analysis of a band position by electrophoresis (comparison with a linear nucleic acid molecule), or the evaluation of annealing to TCNA (appropriate annealing does not occur if a duplex is formed).

In the nucleic acid molecule dimer of the present disclosure, the TCNA and the TNNA at least partially form a duplex region (also referred to as a complementary bond region). The "duplex region" refers to a region where the nucleic acid residues of complementary or substantially complementary two nucleic acid molecules form a hydrogen bond through Watson-Crick base pairing, or a region where complementary or substantially complementary two nucleic acid molecules are attached by any of other methods capable of forming a duplex therebetween. In some embodiments, the duplex region is formed over the entire length of the TCNA and/or the TNNA. In such embodiments, for example, the duplex region is formed over the entire lengths of both the TCNA and the TNNA when the TCNA and the TNNA have the same length, formed over the entire length of the TNNA when the TCNA is longer than the TNNA, and formed over the entire length of the TCNA when the TNNA is longer than the TCNA.

In other embodiments, the duplex region is formed in a portion of both the nucleic acid molecules. 100% complementarity within the duplex region is not necessary, and substantial complementarity is accepted. The substantial complementarity refers to complementarity between nucleic acid molecules that can be annealed under biological conditions. A technique of experimentally determining whether two nucleic acid molecules can be annealed under biological conditions is well known in the art. Alternatively, two nucleic acid molecules can be synthesized and reacted under biological conditions to determine the presence or absence of their annealing. In the nucleic acid molecule dimer of the present disclosure, the length of the duplex region can be approximately 1 to approximately 49 mer, approximately 1 to approximately 30 mer, approximately 15 to approximately 30 mer, etc., though differing depending on the length of each nucleic acid molecule. In a particular embodiment, the length of the duplex region can be 9, 10, 11, 12, 13, 14, 15, 16, 17, 18, 19, 20, 21, 22, 23, 24, 25, 26, 27, 28, 29 or 30 mer, etc. The nucleic acid molecule dimer of the present disclosure typically has a single duplex region and may have a plurality of duplex regions. All the nucleic acid residues in the duplex region typically form a hydrogen bond through Watson-Crick base pairing, while non-hydrogen-bonded nucleic acid residues may form a bulge loop, an internal loop, a branch loop, or the like.

In some embodiments, the TCNA in the nucleic acid molecule dimer of the present disclosure is longer than the TNNA and forms a nick. In the nucleic acid molecule dimer of the present disclosure, the phrase "TCNA forms a nick" means that when the TCNA overlaps with the TNNA via duplex formation and is viewed so as to cover the TNNA, the bond between two consecutive monomers of the TNNA is not covered with the TCNA. Non-limiting examples of the nick include the space between a 3'-terminal nucleotide and nucleotides at the base of a 5' overhang in TCNA shown in A1 of FIG. 1, the space between a 5'-terminal nucleotide and nucleotides at the base of a 3' overhang in TCNA shown in B1 of FIG. 1, the space between nucleotides at the base of a 5' overhang and nucleotides at the base of a 3' overhang in TCNA shown in C3 of FIG. 1, and the space between a 5'-terminal nucleotide and a 3'-terminal nucleotide in TCNA shown in D1 of FIG. 1.

In such embodiments, it is preferred that: the 5'-terminal portion and the 3'-terminal portion of the TCNA should form no duplex (stem); the TCNA should not form a bulge loop and/or a branch loop; neither the TCNA nor the TNNA should form an internal loop; and/or the TCNA should not form a gap. In the nucleic acid molecule dimer of the present disclosure, the phrase "TCNA forms a gap" means that, for example, when two nucleotides of the TCNA form a base pair with respective nucleotides positioned at the ends of a region formed by three or more consecutive nucleotides of the TNNA, these two nucleotides of the TCNA are not associated with each other; and when the TCNA overlaps with the TNNA through duplex formation and is viewed so as to cover the TNNA, the bonds between three or more consecutive monomers of the TNNA are not covered with the TCNA. Non-limiting examples of the gap include the space between nucleotides at the base of a 3' overhang and a 5'-terminal nucleotide in TCNA shown in G3 of FIG. 1. In one embodiment, at least one of the 5'-terminal portion and the 3'-terminal portion of the TCNA forms a overhang. The length of the overhang is not limited and can be, for example, 1 to 10 mer, 1 to 5 mer, or 1 to 3 mer, more specifically, 1, 2, 3, 4, 5, 6, 7, 8, 9, 10 mer, etc. The overhang can be formed, for example, by establishing a TNNA-mismatched nucleotide at the 5' and/or the 3' end of the TCNA.

In a particular embodiment, the nucleic acid molecule dimer of the present disclosure wherein the TCNA is longer than the TNNA includes 17-mer TCNA and 16-mer TNNA, 18-mer TCNA and 16-mer TNNA, 19-mer TCNA and 16-mer TNNA, 20-mer TCNA and 16-mer TNNA, 21-mer TCNA and 16-mer TNNA, 22-mer TCNA and 16-mer TNNA, 23-mer TCNA and 16-mer TNNA, 24-mer TCNA and 16-mer TNNA, 25-mer TCNA and 16-mer TNNA, 26-mer TCNA and 16-mer TNNA, 27-mer TCNA and 16-mer TNNA, 28-mer TCNA and 16-mer TNNA, 29-mer TCNA and 16-mer TNNA, 30-mer TCNA and 16-mer TNNA, 18-mer TCNA and 17-mer TNNA, 19-mer TCNA and 17-mer TNNA, 20-mer TCNA and 17-mer TNNA, 21-mer TCNA and 17-mer TNNA, 22-mer TCNA and 17-mer TNNA, 23-mer TCNA and 17-mer TNNA, 24-mer TCNA and 17-mer TNNA, 25-mer TCNA and 17-mer TNNA, 26-mer TCNA and 17-mer TNNA, 27-mer TCNA and 17-mer TNNA, 28-mer TCNA and 17-mer TNNA, 29-mer TCNA and 17-mer TNNA, 30-mer TCNA and 17-mer TNNA, 19-mer TCNA and 18-mer TNNA, 20-mer TCNA and 18-mer TNNA, 21-mer TCNA and 18-mer TNNA, 22-mer TCNA and 18-mer TNNA, 23-mer TCNA and 18-mer TNNA, 24-mer TCNA and 18-mer TNNA, 25-mer TCNA and 18-mer TNNA, 26-mer TCNA and 18-mer TNNA, 27-mer TCNA and 18-mer TNNA, 28-mer TCNA and 18-mer TNNA, 29-mer TCNA and 18-mer TNNA, 30-mer TCNA and 18-mer TNNA, 20-mer TCNA and 19-mer TNNA, 21-mer TCNA and 19-mer TNNA, 22-mer TCNA and 19-mer TNNA, 23-mer TCNA and 19-mer TNNA, 24-mer TCNA and 19-mer TNNA, 25-mer TCNA and 19-mer TNNA, 26-mer TCNA and 19-mer TNNA, 27-mer TCNA and 19-mer TNNA, 28-mer TCNA and 19-mer TNNA, 29-mer TCNA and 19-mer TNNA, 30-mer TCNA and 19-mer TNNA, 21-mer TCNA and 20-mer TNNA, 22-mer TCNA and 20-mer TNNA, 23-mer TCNA and 20-mer TNNA, 24-mer TCNA and 20-mer TNNA, 25-mer TCNA and 20-mer TNNA, 26-mer TCNA and 20-mer TNNA, 27-mer TCNA and 20-mer TNNA, 28-mer TCNA and 20-mer TNNA, 29-mer TCNA and 20-mer TNNA, 30-mer TCNA and 20-mer TNNA, 22-mer TCNA and 21-mer TNNA, 23-mer TCNA and 21-mer TNNA, 24-mer TCNA and 21-mer TNNA, 25-mer TCNA and 21-mer TNNA, 26-mer TCNA and 21-mer TNNA, 27-mer TCNA and 21-mer TNNA, 28-mer TCNA and 21-mer TNNA, 29-mer TCNA and 21-mer TNNA, 30-mer TCNA and 21-mer TNNA, 23-mer TCNA and 22-mer TNNA, 24-mer TCNA and 22-mer TNNA, 25-mer TCNA and 22-mer TNNA, 26-mer TCNA and 22-mer TNNA, 27-mer TCNA and 22-mer TNNA, 28-mer TCNA and 22-mer TNNA, 29-mer TCNA and 22-mer TNNA, 30-mer TCNA and 22-mer TNNA, 24-mer TCNA and 23-mer TNNA, 25-mer TCNA and 23-mer TNNA, 26-mer TCNA and 23-mer TNNA, 27-mer TCNA and 23-mer TNNA, 28-mer TCNA and 23-mer TNNA, 29-mer TCNA and 23-mer TNNA, 30-mer TCNA and 23-mer TNNA, 25-mer TCNA and 24-mer TNNA, 26-mer TCNA and 24-mer TNNA, 27-mer TCNA and 24-mer TNNA, 28-mer TCNA and 24-mer TNNA, 29-mer TCNA and 24-mer TNNA, 30-mer TCNA and 24-mer TNNA, 26-mer TCNA and 25-mer TNNA, 27-mer TCNA and 25-mer TNNA, 28-mer TCNA and 25-mer TNNA, 29-mer TCNA and 25-mer TNNA, 30-mer TCNA and 25-mer TNNA, 27-mer TCNA and 26-mer TNNA, 28-mer TCNA and 26-mer TNNA, 29-mer TCNA and 26-mer TNNA, 30-mer TCNA and 26-mer TNNA, 28-mer TCNA and 27-mer TNNA, 29-mer TCNA and 27-mer TNNA, 30-mer TCNA and 27-mer TNNA, 29-mer TCNA and 28-mer TNNA, 30-mer TCNA and 28-mer TNNA, or 30-mer TCNA and 29-mer TNNA.

The relationship between the TCNA and the TNNA in the form of the nucleic acid molecule dimer of the present disclosure in which the TCNA is longer than the TNNA and any one of the 5'-terminal portion and the 3'-terminal portion of the TCNA forms a overhang will be represented by the structural formula below. In the formula, Y represents a nucleotide (which includes an unmodified nucleotide and a modified nucleotide; the same holds true for the description below) constituting the overhang portion, X represents a nucleotide constituting the duplex region, and the numeral represents the number of nucleotides. Also, m is 1 to 10, preferably 1 to 5, n is 5 to 39, preferably 14 to 29, o is 1 to 10, preferably 1 to 5, and n' is 5 to 38, preferably 14 to 28, provided that m+n, n+o and m+n'+o are each independently 15 to 49, preferably 15 to 30. Although circularized TNNA is described as if having a 5' end and a 3' end for the sake of convenience, in actuality, the 5' end and the 3' end are attached through a covalent bond as mentioned above so that the ends are absent. This also holds true for similar structural formulas described below.

```
(A) 5' overhang type
5' Y_mX_n 3' (linear TCNA)

3' X_n 5' (circular TNNA)

(B) 3' overhang type
5' X_nY_o 3' (linear TCNA)

3' X_n 5' (circular TNNA)

(C) 5' and 3' overhang type
5' Y_mX_n'Y_o 3' (linear TCNA)

3' X_n' 5' (circular TNNA)
```

The relationship between the TCNA and the TNNA in some preferred forms of the nucleic acid molecule dimer of the present disclosure will be shown below. Y represents a nucleotide constituting the overhang portion, X represents a nucleotide constituting the duplex region, the upper sequence represents linear TCNA, and the lower sequence represents circular TNNA. FIG. 1 shows schematic views of A1, B1, and C3.

```
(A1) 5' overhang type, 19-mer TCNA, 16-mer TNNA
5' YYYXXXXXXXXXXXXXXXX 3'

3'    XXXXXXXXXXXXXXXX 5'

(A2) 5' overhang type, 20-mer TCNA, 16-mer TNNA
5' YYYYXXXXXXXXXXXXXXXX 3'

3'     XXXXXXXXXXXXXXXX 5'

(A3) 5' overhang type, 21-mer TCNA, 16-mer TNNA
5' YYYYYXXXXXXXXXXXXXXXX 3'

3'      XXXXXXXXXXXXXXXX 5'

(A4) 5' overhang type, 22-mer TCNA, 16-mer TNNA
5' YYYYYYXXXXXXXXXXXXXXXX 3'

3'       XXXXXXXXXXXXXXXX 5'

(A5) 5' overhang type, 23-mer TCNA, 16-mer TNNA
5' YYYYYYYXXXXXXXXXXXXXXXX 3'

3'        XXXXXXXXXXXXXXXX 5'

(A6) 5' overhang type, 24-mer TCNA, 16-mer TNNA
5' YYYYYYYYXXXXXXXXXXXXXXXX 3'

3'         XXXXXXXXXXXXXXXX 5'

(A7) 5' overhang type, 25-mer TCNA, 16-mer TNNA
5' YYYYYYYYYXXXXXXXXXXXXXXXX 3'

3'          XXXXXXXXXXXXXXXX 5'

(A8) 5' overhang type, 20-mer TCNA, 19-mer TNNA
5' YXXXXXXXXXXXXXXXXXXX 3'

3'    XXXXXXXXXXXXXXXXXXX 5'

(A9) 5' overhang type, 21-mer TCNA, 19-mer TNNA
5' YYXXXXXXXXXXXXXXXXXXX 3'

3'     XXXXXXXXXXXXXXXXXXX 5'

(A10) 5' overhang type, 22-mer TCNA, 19-mer TNNA
5' YYYXXXXXXXXXXXXXXXXXXX 3'

3'      XXXXXXXXXXXXXXXXXXX 5'

(A11) 5' overhang type, 23-mer TCNA, 19-mer TNNA
5' YYYYXXXXXXXXXXXXXXXXXXX 3'

3'       XXXXXXXXXXXXXXXXXXX 5'

(A12) 5' overhang type, 24-mer TCNA, 19-mer TNNA
5' YYYYYXXXXXXXXXXXXXXXXXXX 3'

3'        XXXXXXXXXXXXXXXXXXX 5'

(A13) 5' overhang type, 25-mer TCNA, 19-mer TNNA
5' YYYYYYXXXXXXXXXXXXXXXXXXX 3'

3'         XXXXXXXXXXXXXXXXXXX 5'

(B1) 3' overhang type, 19-mer TCNA, 16-mer TNNA
5' XXXXXXXXXXXXXXXXYYY 3'

3' XXXXXXXXXXXXXXXX    5'

(B2) 3' overhang type, 20-mer TCNA, 16-mer TNNA
5' XXXXXXXXXXXXXXXXYYYY 3'

3' XXXXXXXXXXXXXXXX     5'

(B3) 3' overhang type, 21-mer TCNA, 16-mer TNNA
5' XXXXXXXXXXXXXXXXYYYYY 3'

3' XXXXXXXXXXXXXXXX      5'

(B4) 3' overhang type, 22-mer TCNA, 16-mer TNNA
5' XXXXXXXXXXXXXXXXYYYYYY 3'

3' XXXXXXXXXXXXXXXX       5'

(B5) 3' overhang type, 23-mer TCNA, 16-mer TNNA
5' XXXXXXXXXXXXXXXXYYYYYYY 3'

3' XXXXXXXXXXXXXXXX        5'

(B6) 3' overhang type, 24-mer TCNA, 16-mer TNNA
5' XXXXXXXXXXXXXXXXYYYYYYYY 3'

3' XXXXXXXXXXXXXXXX         5'

(B7) 3' overhang type, 25-mer TCNA, 16-mer TNNA
5' XXXXXXXXXXXXXXXXYYYYYYYYY 3'

3' XXXXXXXXXXXXXXXX          5'

(B8) 3' overhang type, 20-mer TCNA, 19-mer TNNA
5' XXXXXXXXXXXXXXXXXXXY 3'

3' XXXXXXXXXXXXXXXXXXX  5'

(B9) 3' overhang type, 21-mer TCNA, 19-mer TNNA
5' XXXXXXXXXXXXXXXXXXXYY 3'

3' XXXXXXXXXXXXXXXXXXX   5'

(B10) 3' overhang type, 22-mer TCNA, 19-mer TNNA
5' XXXXXXXXXXXXXXXXXXXYYY 3'
```

```
                   -continued
3' XXXXXXXXXXXXXXXXXX    5'

(B11) 3' overhang type, 23-mer TCNA, 19-mer TNNA
5' XXXXXXXXXXXXXXXXXXXYYYY 3'

3' XXXXXXXXXXXXXXXXXXX      5'

(B12) 3' overhang type, 24-mer TCNA, 19-mer TNNA
5' XXXXXXXXXXXXXXXXXXXXYYYY 3'

3' XXXXXXXXXXXXXXXXXXX       5'

(B13) 3' overhang type, 25-mer TCNA, 19-mer TNNA
5' XXXXXXXXXXXXXXXXXXXXYYYYY 3'

3' XXXXXXXXXXXXXXXXXXX        5'

(C1) 5' and 3' overhang type, 19-mer TCNA,
16-mer TNNA
5' YXXXXXXXXXXXXXXXXXY 3'

3'  XXXXXXXXXXXXXXXX   5'

(C2) 5' and 3' overhang type, 20-mer TCNA,
16-mer TNNA
5' YYXXXXXXXXXXXXXXXXXYY 3'

3'   XXXXXXXXXXXXXXXX   5'

(C3) 5' and 3' overhang type, 21-mer TCNA,
16-mer TNNA
5' YYXXXXXXXXXXXXXXXXXYYY 3'

3'    XXXXXXXXXXXXXXXX   5'

(C4) 5' and 3' overhang type, 22-mer TCNA,
16-mer TNNA
5' YYYXXXXXXXXXXXXXXXXXYYY 3'

3'    XXXXXXXXXXXXXXXX    5'

(C5) 5' and 3' overhang type, 23-mer TCNA,
16-mer TNNA
5' YYYXXXXXXXXXXXXXXXXXYYYY 3'

3'     XXXXXXXXXXXXXXXX    5'

(C6) 5' and 3' overhang type, 24-mer TCNA,
16-mer TNNA
5' YYYYXXXXXXXXXXXXXXXXXYYYY 3'

3'      XXXXXXXXXXXXXXXX    5'

(C7) 5' and 3' overhang type, 25-mer TCNA,
16-mer TNNA
5' YYYYXXXXXXXXXXXXXXXXXYYYYY 3'

3'      XXXXXXXXXXXXXXXX     5'

(C8) 5' and 3' overhang type, 21-mer TCNA,
19-mer TNNA
5' YXXXXXXXXXXXXXXXXXXXY 3'

3'  XXXXXXXXXXXXXXXXXXX   5'

(C9) 5' and 3' overhang type, 22-mer TCNA,
19-mer TNNA
5' YXXXXXXXXXXXXXXXXXXXYY 3'

3'  XXXXXXXXXXXXXXXXXXX    5'

(C10) 5' and 3' overhang type, 23-mer TCNA,
19-mer TNNA
5' YYXXXXXXXXXXXXXXXXXXXYY 3'

3'   XXXXXXXXXXXXXXXXXXX    5'

(C11) 5' and 3' overhang type, 24-mer TCNA,
19-mer TNNA
```
```
                   -continued
5' YYXXXXXXXXXXXXXXXXXXXYYY 3'

3'    XXXXXXXXXXXXXXXXXXX     5'

(C12) 5' and 3' overhang type, 25-mer TCNA,
19-mer TNNA
5' YYYXXXXXXXXXXXXXXXXXXXYYY 3'

3'    XXXXXXXXXXXXXXXXXXX     5'
```

While not wishing to be bound by any particular theory, the form in which the TCNA is longer than the TNNA as described above is considered to circumvent off-target effects ascribable to the TNNA because the incorporation of the TCNA into RISC is preferred rather than that of the TNNA even when the TNNA is cleaved with nuclease or the like so that the nucleic acid molecule dimer is linearized.

In some embodiments, the TCNA in the nucleic acid molecule dimer of the present disclosure has the same length as that of TNNA, and the TCNA forms a nick. Thus, in such embodiments, the TCNA does not form any of a overhang, a gap, a bulge loop and a branch loop, and the TCNA does not form a duplex in itself. It is preferred that the TCNA and the TNNA should not form an internal loop. In a particular embodiment, the nucleic acid molecule dimer of the present disclosure wherein the TCNA and the TNNA have the same length includes 17-mer TCNA and 17-mer TNNA, 18-mer TCNA and 18-mer TNNA, 19-mer TCNA and 19-mer TNNA, 20-mer TCNA and 20-mer TNNA, 21-mer TCNA and 21-mer TNNA, 22-mer TCNA and 22-mer TNNA, 23-mer TCNA and 23-mer TNNA, 24-mer TCNA and 24-mer TNNA, 25-mer TCNA and 25-mer TNNA, 26-mer TCNA and 26-mer TNNA, 27-mer TCNA and 27-mer TNNA, 28-mer TCNA and 28-mer TNNA, 29-mer TCNA and 29-mer TNNA, or 30-mer TCNA and 30-mer TNNA.

The relationship between the TCNA and the TNNA in some preferred forms of the nucleic acid molecule dimer of the present disclosure in which the TCNA has the same length as that of the TNNA and forms a nick will be shown below. X represents a nucleotide constituting the duplex region, the upper sequence represents linear TCNA, and the lower sequence represents circular TNNA. FIG. 1 shows a schematic view of D1.

```
(D1) TCNA18mer, 18-mer TNNA
5' XXXXXXXXXXXXXXXXXX 3'

3' XXXXXXXXXXXXXXXXXX 5'

(D2) 19-mer TCNA, 19-mer TNNA
5' XXXXXXXXXXXXXXXXXXX 3'

3' XXXXXXXXXXXXXXXXXXX 5'

(D3) 20-mer TCNA, 20-mer TNNA
5' XXXXXXXXXXXXXXXXXXXX 3'

3' XXXXXXXXXXXXXXXXXXXX 5'

(D4) 21-mer TCNA, 21-mer TNNA
5' XXXXXXXXXXXXXXXXXXXXX 3'

3' XXXXXXXXXXXXXXXXXXXXX 5'

(D5) 22-mer TCNA, 22-mer TNNA
5' XXXXXXXXXXXXXXXXXXXXXX 3'

3' XXXXXXXXXXXXXXXXXXXXXX 5'

(D6) 23-mer TCNA, 23-mer TNNA
5' XXXXXXXXXXXXXXXXXXXXXXX 3'
```

-continued

```
3' XXXXXXXXXXXXXXXXXXXXXXXX 5'

(D7) 24-mer TCNA, 24-mer TNNA
5' XXXXXXXXXXXXXXXXXXXXXXXX 3'

3' XXXXXXXXXXXXXXXXXXXXXXXX 5'

(D8) 25-mer TCNA, 25-mer TNNA
5' XXXXXXXXXXXXXXXXXXXXXXXXX 3'

3' XXXXXXXXXXXXXXXXXXXXXXXXX 5'
```

In some embodiments, the TCNA in the nucleic acid molecule dimer of the present disclosure forms a gap. The length of the gap is not limited and can be, for example, 1 to 10 mer, 1 to 5 mer, or 1 to 3 mer, more specifically, 1, 2, 3, 4, 5, 6, 7, 8, 9, 10 mer, etc. The length of the TCNA may be larger than, smaller than, or the same as that of the TNNA. Any one of the 5'-terminal portion and the 3'-terminal portion of the TCNA may form a overhang. The length of the overhang is not limited and can be, for example, 1 to 10 mer, 1 to 5 mer, or 1 to 3 mer, more specifically, 1, 2, 3, 4, 5, 6, 7, 8, 9, 10 mer, etc. When the length of the TCNA is larger than or the same as that of the TNNA, the 5'-terminal portion and/or the 3'-terminal portion of the TCNA usually forms a overhang. In such embodiments, it is preferred that: the 5'-terminal portion and the 3'-terminal portion of the TCNA should form no duplex; the TCNA should not form a bulge loop and/or a branch loop; and neither the TCNA nor the TNNA should form an internal loop.

In a particular embodiment, the nucleic acid molecule dimer of the present disclosure wherein the TCNA is shorter than the TNNA includes 17-mer TNNA and 16-mer TCNA, 18-mer TNNA and 16-mer TCNA, 19-mer TNNA and 16-mer TCNA, 20-mer TNNA and 16-mer TCNA, 21-mer TNNA and 16-mer TCNA, 22-mer TNNA and 16-mer TCNA, 23-mer TNNA and 16-mer TCNA, 24-mer TNNA and 16-mer TCNA, 25-mer TNNA and 16-mer TCNA, 26-mer TNNA and 16-mer TCNA, 27-mer TNNA and 16-mer TCNA, 28-mer TNNA and 16-mer TCNA, 29-mer TNNA and 16-mer TCNA, 30-mer TNNA and 16-mer TCNA, 18-mer TNNA and 17-mer TCNA, 19-mer TNNA and 17-mer TCNA, 20-mer TNNA and 17-mer TCNA, 21-mer TNNA and 17-mer TCNA, 22-mer TNNA and 17-mer TCNA, 23-mer TNNA and 17-mer TCNA, 24-mer TNNA and 17-mer TCNA, 25-mer TNNA and 17-mer TCNA, 26-mer TNNA and 17-mer TCNA, 27-mer TNNA and 17-mer TCNA, 28-mer TNNA and 17-mer TCNA, 29-mer TNNA and 17-mer TCNA, 30-mer TNNA and 17-mer TCNA, 19-mer TNNA and 18-mer TCNA, 20-mer TNNA and 18-mer TCNA, 21-mer TNNA and 18-mer TCNA, 22-mer TNNA and 18-mer TCNA, 23-mer TNNA and 18-mer TCNA, 24-mer TNNA and 18-mer TCNA, 25-mer TNNA and 18-mer TCNA, 26-mer TNNA and 18-mer TCNA, 27-mer TNNA and 18-mer TCNA, 28-mer TNNA and 18-mer TCNA, 29-mer TNNA and 18-mer TCNA, 30-mer TNNA and 18-mer TCNA, 20-mer TNNA and 19-mer TCNA, 21-mer TNNA and 19-mer TCNA, 22-mer TNNA and 19-mer TCNA, 23-mer TNNA and 19-mer TCNA, 24-mer TNNA and 19-mer TCNA, 25-mer TNNA and 19-mer TCNA, 26-mer TNNA and 19-mer TCNA, 27-mer TNNA and 19-mer TCNA, 28-mer TNNA and 19-mer TCNA, 29-mer TNNA and 19-mer TCNA, 30-mer TNNA and 19-mer TCNA, 21-mer TNNA and 20-mer TCNA, 22-mer TNNA and 20-mer TCNA, 23-mer TNNA and 20-mer TCNA, 24-mer TNNA and 20-mer TCNA, 25-mer TNNA and 20-mer TCNA, 26-mer TNNA and 20-mer TCNA, 27-mer TNNA and 20-mer TCNA, 28-mer TNNA and 20-mer TCNA, 29-mer TNNA and 20-mer TCNA, 30-mer TNNA and 20-mer TCNA, 22-mer TNNA and 21-mer TCNA, 23-mer TNNA and 21-mer TCNA, 24-mer TNNA and 21-mer TCNA, 25-mer TNNA and 21-mer TCNA, 26-mer TNNA and 21-mer TCNA, 27-mer TNNA and 21-mer TCNA, 28-mer TNNA and 21-mer TCNA, 29-mer TNNA and 21-mer TCNA, 30-mer TNNA and 21-mer TCNA, 23-mer TNNA and 22-mer TCNA, 24-mer TNNA and 22-mer TCNA, 25-mer TNNA and 22-mer TCNA, 26-mer TNNA and 22-mer TCNA, 27-mer TNNA and 22-mer TCNA, 28-mer TNNA and 22-mer TCNA, 29-mer TNNA and 22-mer TCNA, 30-mer TNNA and 22-mer TCNA, 24-mer TNNA and 23-mer TCNA, 25-mer TNNA and 23-mer TCNA, 26-mer TNNA and 23-mer TCNA, 27-mer TNNA and 23-mer TCNA, 28-mer TNNA and 23-mer TCNA, 29-mer TNNA and 23-mer TCNA, 30-mer TNNA and 23-mer TCNA, 25-mer TNNA and 24-mer TCNA, 26-mer TNNA and 24-mer TCNA, 27-mer TNNA and 24-mer TCNA, 28-mer TNNA and 24-mer TCNA, 29-mer TNNA and 24-mer TCNA, 30-mer TNNA and 24-mer TCNA, 26-mer TNNA and 25-mer TCNA, 27-mer TNNA and 25-mer TCNA, 28-mer TNNA and 25-mer TCNA, 29-mer TNNA and 25-mer TCNA, 30-mer TNNA and 25-mer TCNA, 27-mer TNNA and 26-mer TCNA, 28-mer TNNA and 26-mer TCNA, 29-mer TNNA and 26-mer TCNA, 30-mer TNNA and 26-mer TCNA, 28-mer TNNA and 27-mer TCNA, 29-mer TNNA and 27-mer TCNA, 30-mer TNNA and 27-mer TCNA, 29-mer TNNA and 28-mer TCNA, 30-mer TNNA and 28-mer TCNA, or 30-mer TNNA and 29-mer TCNA. The particular forms of the nucleic acid molecule dimer of the present disclosure in which the TCNA is longer than the TNNA and the nucleic acid molecule dimer of the present disclosure in which the TCNA has the same length as that of the TNNA are as described above.

The relationship between the TCNA and the TNNA in the form of the nucleic acid molecule dimer of the present disclosure in which the TCNA forms a gap will be represented by the structural formula below. In the formula, Y represents a nucleotide constituting the overhang portion, X represents a nucleotide constituting the duplex region, Z represents a nucleotide of TNNA that forms no base pair with a nucleotide of TCNA due to gap formation in the TCNA, and the numeral represents the number of nucleotides. Also, m is 1 to 10, preferably 1 to 5, n is 5 to 39, preferably 14 to 29, o is 1 to 10, preferably 1 to 5, n' is 5 to 38, preferably 14 to 28, p is 1 to 10, preferably 1 to 5, and q is 1 to 11, preferably 1 to 6, provided that m+n, n+o, m+n'+o, n+p and n'+q are each independently 15 to 49, preferably 15 to 30. Although Zp and Zq are described on the 5' side of TNNA for the sake of convenience, actual circular TNNA has neither a 5' end nor a 3' end as described above; thus Zp and Zq may be regarded as being positioned at the 3' end.

(E) Gap and non-overhang type

```
(linear TCNA)
5'  X_n  3'

(circular TNNA)
3'  X_n Z_p  5'
```

(F) Gap and 5' overhang type
(linear TCNA)

```
5' Y_m X_n 3'

(circular TNNA)
3' X_n Z_p 5'

(G) Gap and 3' overhang type
(linear TCNA)
5' X_n Y_o 3'

(circular TNNA)
3' X_n Z_p 5'

(H) Gap and 5' and 3' overhang type
(linear TCNA)
5' Y_m X_n, Y_o 3'

(circular TNNA)
3' X_n, Z_q 5'
```

The relationship between the TCNA and the TNNA in some preferred forms of the nucleic acid molecule dimer of the present disclosure will be shown below. Y represents a nucleotide constituting the overhang portion, X represents a nucleotide constituting the duplex region, Z represents a nucleotide of TNNA that forms no base pair with a nucleotide of TCNA due to gap formation in the TCNA, the upper sequence represents linear TCNA, and the lower sequence represents circular TNNA. FIG. 1 shows a schematic view of G3.

```
(E1) Gap and non-overhang type, 19-mer TCNA,
21-mer TNNA
5' XXXXXXXXXXXXXXXXXXX 3'

3' XXXXXXXXXXXXXXXXXXXZZ 5'

(E2) Gap and non-overhang type, 19-mer TCNA,
23-mer TNNA
5' XXXXXXXXXXXXXXXXXXX 3'

3' XXXXXXXXXXXXXXXXXXXZZZZ 5'

(E3) Gap and non-overhang type, 19-mer TCNA,
25-mer TNNA
5' XXXXXXXXXXXXXXXXXXX 3'

3' XXXXXXXXXXXXXXXXXXXZZZZZZ 5'

(E4) Gap and non-overhang type, 21-mer TCNA,
23-mer TNNA
5' XXXXXXXXXXXXXXXXXXXXX 3'

3' XXXXXXXXXXXXXXXXXXXXXZZ 5'

(E5) Gap and non-overhang type, 21-mer TCNA,
25-mer TNNA
5' XXXXXXXXXXXXXXXXXXXXX 3'

3' XXXXXXXXXXXXXXXXXXXXXZZZZ 5'

(F1) Gap and 5' overhang type, 19-mer TCNA,
19-mer TNNA
5' YYYXXXXXXXXXXXXXXXX 3'

3'    XXXXXXXXXXXXXXXXZZZ 5'

(F2) Gap and 5' overhang type, 19-mer TCNA,
18-mer TNNA
5' YYYXXXXXXXXXXXXXXXX 3'

3'    XXXXXXXXXXXXXXXXZZ 5'

(F3) Gap and 5' overhang type, 19-mer TCNA,
16-mer TNNA
5' YYYYXXXXXXXXXXXXXXX 3'

3'    XXXXXXXXXXXXXXXZ 5'

(F4) Gap and 5' overhang type, 21-mer TCNA,
21-mer TNNA
5' YYYXXXXXXXXXXXXXXXXXX 3'

3'    XXXXXXXXXXXXXXXXXXZZZ 5'

(F5) Gap and 5' overhang type, 21-mer TCNA,
19-mer TNNA
5' YYYXXXXXXXXXXXXXXXXXX 3'

3'    XXXXXXXXXXXXXXXXXXZ 5'

(F6) Gap and 5' overhang type, 21-mer TCNA,
18-mer TNNA
5' YYYYXXXXXXXXXXXXXXXXX 3'

3'    XXXXXXXXXXXXXXXXXZ 5'

(F7) Gap and 5' overhang type, 21-mer TCNA,
16-mer TNNA
5' YYYYYYXXXXXXXXXXXXXXX 3'

3'      XXXXXXXXXXXXXXXZ 5'

(G1) Gap and 3' overhang type, 19-mer TCNA,
19-mer TNNA
5' XXXXXXXXXXXXXXXXYYY 3'

3' XXXXXXXXXXXXXXXXZZZ 5'

(G2) Gap and 3' overhang type, 19-mer TCNA,
18-mer TNNA
5' XXXXXXXXXXXXXXXXYYY 3'

3' XXXXXXXXXXXXXXXXZZ 5'

(G3) Gap and 3' overhang type, 19-mer TCNA,
16-mer TNNA
5' XXXXXXXXXXXXXXXYYYY 3'

3' XXXXXXXXXXXXXXXZ 5'

(G4) Gap and 3' overhang type, 21-mer TCNA,
21-mer TNNA
5' XXXXXXXXXXXXXXXXXXYYY 3'

3' XXXXXXXXXXXXXXXXXXZZZ 5'

(G5) Gap and 3' overhang type, 21-mer TCNA,
19-mer TNNA
5' XXXXXXXXXXXXXXXXXXYYY 3'

3' XXXXXXXXXXXXXXXXXXZ 5'

(G6) Gap and 3' overhang type, 21-mer TCNA,
18-mer TNNA
5' XXXXXXXXXXXXXXXXXYYYY 3'

3' XXXXXXXXXXXXXXXXXZ 5'

(G7) Gap and 3' overhang type, 21-mer TCNA,
16-mer TNNA
5' XXXXXXXXXXXXXXXYYYYYY 3'

3' XXXXXXXXXXXXXXXZ 5'

(H1) Gap and 5' and 3' overhang type,
19-mer TCNA, 19-mer TNNA
5' YXXXXXXXXXXXXXXXXXY 3'

3'  XXXXXXXXXXXXXXXXZZZ 5'

(H2) Gap and 5' and 3' overhang type,
19-mer TCNA, 18-mer TNNA
5' YYXXXXXXXXXXXXXXXXY 3'

3'   XXXXXXXXXXXXXXXXZZZ 5'

(H3) Gap and 5' and 3' overhang type,
19-mer TCNA, 16-mer TNNA
```

```
                       -continued
5' YYXXXXXXXXXXXXXXXXYYY 3'

3'    XXXXXXXXXXXXXXXZZ 5'

(H4) Gap and 5' and 3' overhang type,
21-mer TCNA, 21-mer TNNA
5' YXXXXXXXXXXXXXXXXXXXY 3'

3'    XXXXXXXXXXXXXXXXXZZZ 5'

(H5) Gap and 5' and 3' overhang type,
21-mer TCNA, 19-mer TNNA
5' YYXXXXXXXXXXXXXXXXXYY 3'

3'    XXXXXXXXXXXXXXXXXZZ 5'

(H6) Gap and 5' and 3' overhang type,
21-mer TCNA, 18-mer TNNA
5' YYXXXXXXXXXXXXXXXXXYY 3'

3'    XXXXXXXXXXXXXXXXXZ 5'

(H7) Gap and 5' and 3' overhang type,
21-mer TCNA, 16-mer TNNA
5' YYYXXXXXXXXXXXXXXXYYY 3'

3'     XXXXXXXXXXXXXXXZ 5'
```

The TCNA and the TNNA in the nucleic acid molecule dimer of the present disclosure may comprise an unmodified nucleotide and/or a modified nucleotide. In the present specification, the unmodified nucleotide and the modified nucleotide are simply referred to as a "nucleotide" collectively. The unmodified nucleotide refers to a naturally occurring nucleotide constituting DNA or RNA, i.e., a substance constituted by a nucleobase (adenine, guanine, uracil, thymine, or cytosine), a sugar (ribose or deoxyribose), and a phosphate group. In an unmodified nucleic acid molecule constituted by unmodified nucleotides, the 3' position of one of two adjacent unmodified nucleotides is usually linked to the 5' position of the other unmodified nucleotide through a phosphodiester bond. The unmodified nucleotide may be an unmodified ribonucleotide or an unmodified deoxyribonucleotide. The unmodified nucleic acid molecule may be constituted by unmodified ribonucleotides alone, unmodified deoxyribonucleotides alone, or both unmodified ribonucleotides and unmodified deoxyribonucleotides.

The modified nucleotide refers to a nucleotide containing a chemical modification to the unmodified nucleotide. The modified nucleotide may be artificially synthesized or may occur naturally. The modified nucleotide includes a nucleotide modified at its nucleobase, sugar, backbone (internucleotide bond), 5' end and/or 3' end. The modified nucleotide also includes a nucleotide modified at any one of these sites as well as a nucleotide modified at two or more of the sites.

Examples of the modification to the nucleobase include, but are not limited to, 2,4-difluorotoluyl, 2,6-diamino, 5-bromo, 5-iodo, 2-thio, dihydro, 5-propynyl, and 5-methyl modifications, and elimination of a base. Examples of modified nucleobase include, but are not limited to, xanthine, hypoxanthine, inosine, 2-aminoadenine, 6-methyl and other alkyl derivatives of adenine and guanine, universal base, 2-propyl and other alkyl derivatives of adenine and guanine, 5-halouracil and 5-halocytosine, 5-propynyl uracil and 5-propynyl cytosine, 6-azo uracil, 6-azo cytosine and 6-azo thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine, acyclonucleotides, deazapurines, heterocyclic substituted analogs of purines and pyrimidines, e.g., aminoethyoxy phenoxazine, derivatives of purines and pyrimidines (e.g., 1-alkyl-, 1-alkenyl-, heteroaromatic- and 1-alkynyl derivatives) and tautomers thereof, 8-oxo-N6-methyladenine, 7-diazaxanthine, 5-methylcytosine, 5-methyluracil, 5-(1-propynyl) uracil, 5-(1-propynyl) cytosine and 4,4-ethanocytosine, non-purinyl and non-pyrimidinyl bases such as 2-aminopyridine and triazines, abasic nucleotide, deoxy abasic nucleotide, inverted abasic nucleotide, inverted deoxy abasic nucleotide, and the like.

Examples of the modification to the sugar include, but are not limited to: modifications at position 2', for example, 2'-O-alkyl modifications (e.g., 2'-O-methyl modification and 2'-O-ethyl modification), 2'-methoxyethoxy modification, 2'-methoxyethyl modification, 2'-deoxy modification, 2'-halogen modifications (2'-fluoro modification, 2'-chloro modification, 2'-bromo modification, etc.), 2'-O-allyl modification, 2'-amino modification, 2'-S-alkyl modification, 2'-O-[2(methylamino)-2-oxoethyl] modification, 2'-alkoxy modification, 2'-O-2-methoxyethyl, 2'-allyloxy ($—OCH_2CH=CH_2$), 2'-propargyl, 2'-propyl, 2'-O—(N-methyl carbamate) modification, 2'-O-(2,4-dinitrophenyl) modification, and 2'-deoxy-2'-fluoro-β-D-arabino modification; modifications at position 4', for example, 4'-thio modification and 4'-C-hydroxymethyl modification; and other modifications with ethynyl, ethenyl, propenyl, CF, cyano, imidazole, carboxylate, thioate, $C_1$ to $C_{10}$ lower alkyl, substituted lower alkyl, alkaryl or aralkyl, $OCF_3$, OCN, O-, S- or N-alkyl, O-, S- or N-alkenyl, $SOCH_3$, $SO_2CH_3$, $ONO_2$, $NO_2$, $N_3$, heterocycloalkyl, heterocycloalkaryl, aminoalkylamino, polyalkylamino or substituted silyl. Other examples of the modified sugar include locked nucleic acid (LNA), oxetane-LNA (OXE), unlocked nucleic acid (UNA), ethylene-bridged nucleic acid (ENA), altriol nucleic acid (ANA), and hexitol nucleic acid (HNA).

In the present disclosure, alkyl group includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), and alkyl substituted cycloalkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls may have from 3-8 carbon atoms in their ring structure, and more preferably have 5 or 6 carbons in the ring structure. The term $C_1$-$C_6$ includes alkyl groups containing 1 to 6 carbon atoms. The alkyl group can be substituted alkyl group such as alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

In the present disclosure, alkoxy group includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

In the present disclosure, halogens include fluorine, bromine, chlorine, iodine.

Examples of modified backbone include, but are not limited to phosphorothioate, thiophosphate-D-ribose entities, triester, thioate, 2'-5' bridged backbone (may also be referred to as 5'-2' or 2'5' nucleotide or 2'5' ribonucleotide), PACE, 3'-(or -5')deoxy-3'-(or -5')thio-phosphorothioate, phosphorodithioate, phosphoroselenates, 3'-(or -5')deoxy phosphinates, borano phosphates, 3'-(or -5')deoxy-3'-(or 5'-) amino phosphoramidates, hydrogen phosphonates, phosphonates, borano phosphate esters, phosphoramidates, alkyl or aryl phosphonates and phosphotriester modifications such as alkylphosphotriesters, phosphotriester phosphorus linkages, 5'-ethoxyphosphodiester, P-alkyloxyphosphotriester, methylphosphonate, and nonphosphorus containing linkages for example, carbonate, carbamate, silyl, sulfur, sulfonate, sulfonamide, formacetal, thioformacetyl, oxime, methyleneimino, methylenemethylimino, methylenehydrazo, methylenedimethylhydrazo and methyleneoxymethylimino linkages.

Examples of 5'- and/or 3'-end modification include addition of a capping moiety to 5'- and/or 3'-end, and modification at terminal phosphate groups, such as [3-3']-inverted deoxyribose, deoxyribonucleotide, [5'-3']-3'-deoxyribonucleotide, [5'-3']-ribonucleotide, [5'-3']-3'-O-methyl ribonucleotide, 3'-glyceryl, [3'-5']-3'-deoxyribonucleotide, [3'-3']-deoxyribonucleotide, [5'-2']-deoxyribonucleotide, and [5-3']-dideoxyribonucleotide. Non-limiting examples of capping moiety include an abasic nucleotide, a deoxy abasic nucleotide, an inverted (deoxy) abasic nucleotide, a hydrocarbon (alkyl) moiety and derivatives thereof, a mirror nucleotide (L-DNA or L-RNA), bridged nucleic acids including LNA and ethylene bridged nucleic acids, linkage modified nucleotides (e.g. PACE) and base modified nucleotides, glyceryl, dinucleotide, acyclic nucleotide, amino, fluoro, chloro, bromo, CN, CF, methoxy, imidazole, carboxylate, thioate, $C_1$ to $C_{10}$ lower alkyl, substituted lower alkyl, alkaryl or aralkyl, $OCF_3$, OCN, O, S, or N-alkyl, O, S, or N-alkenyl, $SOCH_3$, $SO_2CH_3$, $ONO_2$, $NO_2$, $N_3$, heterocycloalkyl, heterocycloalkaryl, aminoalkylamino, polyalkylamino or substituted silyl. The capping moiety may serve as a non-nucleotide overhang.

Modified nucleotides of the present disclosure include 2'-deoxyribonucleotides, 2'-O-methyl ribonucleotides, 2'-deoxy-2'-fluoro ribonucleotides, universal base nucleotides, acyclic nucleotides, 5-C-methyl nucleotides, nucleotides containing biotin group, and terminal glyceryl and/or inverted deoxy abasic residue, nucleotide containing sterically hindered molecules, such as fluorescent molecules and the like, 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T), nucleotides containing 3'-azido-3'-deoxythymidine (AZT), 2',3'-dideoxy-3'-thiacytidine (3TC) or 2',3'-didehydro-2',3'-dide-oxythymidine (d4T), a nucleotide having a Northern conformation, 2'-methyl-thio-ethyl, 2'-deoxy-2'-fluoro nucleotides, 2'-deoxy-2'-chloro nucleotides, 2'-azido nucleotides, and 2'-O-methyl nucleotides, 6-membered ring nucleotide analogs including hexitol and altritol nucleotide monomers disclosed in WO 2006/047842, etc., mirror nucleotides (for example L-DNA (L-deoxyriboadenosine-3'-phosphate (mirror dA), L-deoxyribocytidine-3'-phosphate (mirror dC), L-deoxyriboguanosine-3'-phosphate (mirror dG), L-deoxyribothymidine-3'-phosphate (mirror image dT)) and L-RNA (L-riboadenosine-3'-phosphate (mirror rA), L-ribocytidine-3'-phosphate (mirror rC), L-riboguanosine-3'-phosphate (mirror rG), L-ribouracil-3'-phosphate (mirror dU), etc.).

Non-limiting examples of the modified nucleotide are also described in, for example, Gaglione and Messere, Mini Rev Med Chem. 2010; 10 (7): 578-95, Deleavey and Damha, Chem Biol. 2012; 19 (8): 937-54, and Bramsen and Kjems, J. Front Genet. 2012; 3: 154.

In some embodiments, the TCNA and/or the TNNA in the nucleic acid molecule dimer of the present disclosure is constituted by unmodified nucleotides and comprises no modified nucleotide. In other embodiments, the TCNA and/or the TNNA in the nucleic acid molecule dimer of the present disclosure comprises both unmodified nucleotides and modified nucleotides. In other embodiments, the TCNA and/or the TNNA in the nucleic acid molecule dimer of the present disclosure is constituted by modified nucleotides and comprises no unmodified nucleotide.

The nucleic acid molecule dimer of the present disclosure comprising modified nucleotides may have at least one of the modifications described above and may have a combination of two or more of the modifications described above. The modification may be present in one or two or more nucleic acid molecules, for example, the TNNA, the TCNA or both, in the nucleic acid molecule dimer disclosed in the present specification. In some embodiments, the TCNA may comprise modified nucleotides, and the TNNA may comprise unmodified nucleotides alone. In other embodiments, the TCNA may comprise unmodified nucleotides alone, and the TNNA may comprise modified nucleotides. The nucleic acid molecule dimer of the present disclosure may comprise approximately 5% to approximately 100% of unmodified nucleotides (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% of unmodified nucleotides) with respect to all the nucleotides in the nucleic acid molecule(s). Also, the nucleic acid molecule dimer of the present disclosure may comprise approximately 5% to approximately 100% of modified nucleotides (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% of modified nucleotides) with respect to all the nucleotides in the nucleic acid molecule(s). The actual percentage of unmodified nucleotides or modified nucleotides present in the nucleic acid molecule(s) depends on the total number of nucleotides present in the nucleic acid molecule(s). The percentage of unmodified nucleotides or modified nucleotides (non-modification or modification percent) can be based on the total number of nucleotides present in the TNNA, the TCNA or both the TNNA and the TCNA.

In some embodiments, the modification may be used for enhancing the target nucleic acid molecule expression modulatory activity of the nucleic acid molecule of the present disclosure, and/or for enhancing the in vivo stability, particularly, stability in serum, of the nucleic acid molecule, and/or for enhancing the bioavailability of the nucleic acid molecule.

Particular non-limiting examples of the nucleic acid molecule dimer of the present disclosure are described in Table 3.

The nucleic acid molecule dimer of the present disclosure may or may not be labeled. The labeling permits monitoring of success and failure of delivery to a target site, an in vivo position, etc., and such a labeled nucleic acid molecule dimer is also useful not only in tests and research but in clinical application. The label can be selected from arbitrary labels known to those skilled in the art, for example, an arbitrary radioisotope, a magnetic body, a gas or a substance that generates a gas under physiological conditions, a nuclear magnetic resonant element (e.g., hydrogen, phosphorus, sodium, and fluorine), a substance that influences the relaxation time of a nuclear magnetic resonant element (e.g., metal atoms or compounds containing the metal atoms), a substance binding to a labeling material (e.g., antibodies), a fluorescent material, a fluorophore, a chemiluminescent material, biotin or its derivative, avidin or its derivative, and an enzyme.

The nucleic acid molecule dimer of the present disclosure can modulate the expression of a target nucleic acid molecule in a sequence-specific manner. The expression of the target nucleic acid molecule includes the exertion of a function of the target nucleic acid molecule. Thus, the expression of the target nucleic acid molecule includes, for example, the formation of an expression product when the target nucleic acid molecule encodes the expression product (e.g., a protein and a nucleic acid molecule such as a RNA molecule), and includes the exertion of biological activity when the target nucleic acid molecule has the biological activity in itself. The modulation of expression of the target nucleic acid molecule includes the modulation of formation of an expression product encoded by the target nucleic acid molecule, and the modulation of biological activity possessed by the target nucleic acid molecule. The modulation of expression includes the suppression of expression and increase in expression. When the expression level of the target nucleic acid molecule without the action of the nucleic acid molecule dimer of the present disclosure is used as a reference, the degree of modulation in terms of the expression level of the target nucleic acid molecule by the action of the nucleic acid molecule dimer of the present disclosure can be approximately ±50% or more, preferably approximately ±60% or more, more preferably approximately ±65% or more, further preferably approximately ±70% or more, particularly preferably approximately ±75% or more, of the reference value. Thus, the nucleic acid molecule dimer of the present disclosure can be used for modulating the expression of the target nucleic acid molecule. When the expression of the target nucleic acid molecule is related to a disease, the nucleic acid molecule dimer of the present disclosure can be used for treating a disease associated with the expression of the target nucleic acid molecule.

In some embodiments, the nucleic acid molecule dimer of the present disclosure can suppress the expression of a target nucleic acid molecule by RNA silencing. When the expression level of the target nucleic acid molecule without the action of the nucleic acid molecule dimer of the present disclosure is defined as 100%, the degree of suppression in terms of the expression level of the target nucleic acid molecule by the action of the nucleic acid molecule dimer of the present disclosure can be approximately 50% or less, preferably approximately 40% or less, more preferably approximately 35% or less, further preferably approximately 30% or less, particularly preferably approximately 25% or less. In such embodiments, the nucleic acid molecule dimer of the present disclosure can be used for suppressing the expression of the target nucleic acid molecule. When the expression of the target nucleic acid molecule is related to a disease and when the suppression of expression of the target nucleic acid molecule is useful in improvement in the disease, this form of the nucleic acid molecule dimer of the present disclosure can be used for treating a disease associated with the expression of the target nucleic acid molecule.

In other embodiments, the nucleic acid molecule dimer of the present disclosure can increase the expression of a target nucleic acid molecule by RNAa. When the expression level of the target nucleic acid molecule without the action of the nucleic acid molecule dimer of the present disclosure is defined as 100%, the degree of increase in terms of the expression level of the target nucleic acid molecule by the action of the nucleic acid molecule dimer of the present disclosure can be approximately 120% or more, preferably approximately 130% or more, more preferably approximately 150% or more, further preferably approximately 180% or more, particularly preferably approximately 200% or more. In such embodiments, the nucleic acid molecule dimer of the present disclosure can be used for increasing the expression of the target nucleic acid molecule. When the expression of the target nucleic acid molecule is related to a disease and when the increase in the expression of the target nucleic acid molecule is useful in improvement in the disease, this form of the nucleic acid molecule dimer of the present disclosure can be used for treating a disease associated with the expression of the target nucleic acid molecule.

In some embodiments, the nucleic acid molecule dimer of the present disclosure produces less off-target effects ascribable to TNNA. More specifically, the nucleic acid molecule dimer of the present disclosure produces less off-target effects ascribable to TNNA, as compared with a nucleic acid molecule dimer that is similar thereto but has non-circular TNNA, for example, a nucleic acid molecule dimer that is similar thereto (e.g., having the same nucleotide sequence thereas) but has linear TNNA. Thus, the TNNA in the nucleic acid molecule dimer of the present disclosure has less need for devising sequence design, for example, in order to circumvent off-target effects. In such embodiments, the nucleic acid molecule dimer of the present disclosure can be used for modulating the expression of the target nucleic acid molecule while circumventing off-target effects ascribable to TNNA. When the expression of the target nucleic acid molecule is related to a disease, this form of the nucleic acid molecule dimer of the present disclosure can be used for treating a disease associated with the expression of the target nucleic acid molecule while circumventing off-target effects ascribable to TNNA. When the nucleic acid molecule dimer of the present disclosure can suppress the expression of the target nucleic acid molecule by RNA silencing or the like, this form of the nucleic acid molecule dimer of the present disclosure can be used for suppressing the expression of the target nucleic acid molecule while circumventing off-target effects ascribable to TNNA. When the expression of the target nucleic acid molecule is related to a disease and when the suppression of expression of the target nucleic acid molecule is useful in improvement in the disease, this form of the nucleic acid molecule dimer of the present disclosure can be used for treating a disease associated with the expression of the target nucleic acid molecule while circumventing off-target effects ascribable to TNNA. When the nucleic acid molecule dimer of the present disclosure can increase the expression of the target nucleic acid molecule by RNAa or the like, this form of the nucleic acid molecule dimer of the present disclosure can be used for increasing the expression of the target nucleic acid molecule while circumventing off-target effects ascribable to TNNA. When the expression of the target nucleic acid molecule is related to a disease and when the increase in the expression of the target nucleic acid molecule is useful in improvement in the disease, this form of the nucleic acid molecule dimer of the present disclosure can be used for treating a disease associated with the expression of the target nucleic acid molecule while circumventing off-target effects ascribable to TNNA.

In some embodiments, the nucleic acid molecule dimer of the present disclosure, when administered to cells, can circumvent the phosphorylation of PKR (double-stranded RNA-dependent protein kinase). Specifically, the nucleic acid molecule dimer of the present disclosure, even if administered to cells, does not induce the phosphorylation of PKR or induces the phosphorylation of PKR to a low degree as compared with a nucleic acid molecule dimer that is similar thereto but has non-circular TNNA, for example, a nucleic acid molecule dimer that is similar thereto (e.g., having the same nucleotide sequence thereas) but has linear TNNA. In such embodiments, the nucleic acid molecule dimer of the present disclosure can be used for modulating the expression of the target nucleic acid molecule while circumventing the phosphorylation of PKR. When the expression of the target nucleic acid molecule is related to a disease, this form of the nucleic acid molecule dimer of the present disclosure can be used for treating a disease associated with the expression of the target nucleic acid molecule while circumventing the phosphorylation of PKR. When the nucleic acid molecule dimer of the present disclosure can suppress the expression of the target nucleic acid molecule by RNA silencing or the like, this form of the nucleic acid molecule dimer of the present disclosure can be used for suppressing the expression of the target nucleic acid molecule while circumventing the phosphorylation of PKR. When the expression of the target nucleic acid molecule is related to a disease and when the suppression of expression of the target nucleic acid molecule is useful in improvement in the disease, this form of the nucleic acid molecule dimer of the present disclosure can be used for treating a disease associated with the expression of the target nucleic acid molecule while circumventing the phosphorylation of PKR. When the nucleic acid molecule dimer of the present disclosure can increase the expression of the target nucleic acid molecule by RNAa or the like, this form of the nucleic acid molecule dimer of the present disclosure can be used for increasing the expression of the target nucleic acid molecule while circumventing the phosphorylation of PKR. When the expression of the target nucleic acid molecule is related to a disease and when the increase in the expression of the target nucleic acid molecule is useful in improvement in the disease, this form of the nucleic acid molecule dimer of the present disclosure can be used for treating a disease associated with the expression of the target nucleic acid molecule while circumventing the phosphorylation of PKR.

In some embodiments, the nucleic acid molecule dimer of the present disclosure, when administered to cells, can circumvent the activation of the TLR3 pathway. Specifically, the nucleic acid molecule dimer of the present disclosure, even if administered to cells, does not induce the activation of the TLR3 pathway or induces the activation of the TLR3 pathway to a low degree as compared with a nucleic acid molecule dimer that is similar thereto but has non-circular TNNA, for example, a nucleic acid molecule dimer that is similar thereto (e.g., having the same nucleotide sequence thereas) but has linear TNNA. In such embodiments, the nucleic acid molecule dimer of the present disclosure can be used for modulating the expression of the target nucleic acid molecule while circumventing the activation of the TLR3 pathway. When the expression of the target nucleic acid molecule is related to a disease, this form of the nucleic acid molecule dimer of the present disclosure can be used for treating a disease associated with the expression of the target nucleic acid molecule while circumventing the activation of the TLR3 pathway. When the nucleic acid molecule dimer of the present disclosure can suppress the expression of the target nucleic acid molecule by RNA silencing or the like, this form of the nucleic acid molecule dimer of the present disclosure can be used for suppressing the expression of the target nucleic acid molecule while circumventing the activation of the TLR3 pathway. When the expression of the target nucleic acid molecule is related to a disease and when the suppression of expression of the target nucleic acid molecule is useful in improvement in the disease, this form of the nucleic acid molecule dimer of the present disclosure can be used for treating a disease associated with the expression of the target nucleic acid molecule while circumventing the activation of the TLR3 pathway. When the nucleic acid molecule dimer of the present disclosure can increase the expression of the target nucleic acid molecule by RNAa or the like, this form of the nucleic acid molecule dimer of the present disclosure can be used for increasing the expression of the target nucleic acid molecule while circumventing the activation of the TLR3 pathway. When the expression of the target nucleic acid molecule is related to a disease and when the increase in the expression of the target nucleic acid molecule is useful in improvement in the disease, this form of the nucleic acid molecule dimer of the present disclosure can be used for treating a disease associated with the expression of the target nucleic acid molecule while circumventing the activation of the TLR3 pathway.

In a particular embodiment, the nucleic acid molecule dimer of the present disclosure, when administered to cells, can circumvent off-target effects ascribable to TNNA, the phosphorylation of PKR and the activation of the TLR3 pathway. Thus, in such embodiments, the nucleic acid molecule dimer of the present disclosure can be used for modulating the expression of the target nucleic acid molecule while circumventing off-target effects ascribable to TNNA, the phosphorylation of PKR and the activation of the TLR3 pathway. When the expression of the target nucleic acid molecule is related to a disease, this form of the nucleic acid molecule dimer of the present disclosure can be used for treating a disease associated with the expression of the target nucleic acid molecule while circumventing off-target effects ascribable to TNNA, the phosphorylation of PKR and the activation of the TLR3 pathway. When the nucleic acid molecule dimer of the present disclosure can suppress the expression of the target nucleic acid molecule by RNA silencing or the like, this form of the nucleic acid molecule dimer of the present disclosure can be used for suppressing the expression of the target nucleic acid molecule while circumventing off-target effects ascribable to TNNA, the phosphorylation of PKR and the activation of the TLR3 pathway. When the expression of the target nucleic acid molecule is related to a disease and when the suppression of expression of the target nucleic acid molecule is useful in improvement in the disease, this form of the nucleic acid molecule dimer of the present disclosure can be used for treating a disease associated with the expression of the target nucleic acid molecule while circumventing off-target effects ascribable to TNNA, the phosphorylation of PKR and the activation of the TLR3 pathway. When the nucleic acid molecule dimer of the present disclosure can increase the expression of the target nucleic acid molecule by RNAa or the like, this form of the nucleic acid molecule dimer of the present disclosure can be used for increasing the expression of the target nucleic acid molecule while circumventing off-target effects ascribable to TNNA, the phosphorylation of PKR and the activation of the TLR3 pathway. When the expression of the target nucleic acid molecule is related to a disease and when the increase in the expression of the target nucleic acid molecule is useful in improvement in the disease, this form of the nucleic acid molecule dimer of the present disclosure can be used for treating a disease associated with the expression of the target nucleic acid molecule while circumventing off-target effects ascribable to TNNA, the phosphorylation of PKR and the activation of the TLR3 pathway.

PKR is autophosphorylated through sequence-non-specific binding to double-stranded RNA to phosphorylate its substrate such as NF-κB, bringing about the production of interferon or the like. TLR3 is also autophosphorylated through sequence-non-specific binding to double-stranded RNA to phosphorylate its substrate such as NF-κB, bringing about the production of interferon or the like. Thus, PKR and TLR3 are considered to play a role as a sensor molecule positioned most upstream in the process of induction of sequence-non-specific cell response (e.g., natural immunity) by nucleic acid molecules (particularly, double-stranded RNA molecules). The nucleic acid molecule dimer of the present disclosure that can circumvent the phosphorylation of PKR and the activation of the TLR3 pathway can circumvent the induction of such cell response from the most upstream of the process. Thus, in some embodiments, the nucleic acid molecule dimer of the present disclosure can circumvent the induction of sequence-non-specific cell response (e.g., natural immunity) by a nucleic acid molecule. In such embodiments, the nucleic acid molecule dimer of the present disclosure can be used for modulating the expression of the target nucleic acid molecule while circumventing the induction of the cell response. When the expression of the target nucleic acid molecule is related to a disease, this form of the nucleic acid molecule dimer of the present disclosure can be used for treating a disease associated with the expression of the target nucleic acid molecule while circumventing the induction of the cell response. When the nucleic acid molecule dimer of the present disclosure can suppress the expression of the target nucleic acid molecule by RNA silencing or the like, this form of the nucleic acid molecule dimer of the present disclosure can be used for suppressing the expression of the target nucleic acid molecule while circumventing the induction of the cell response. When the expression of the target nucleic acid molecule is related to a disease and when the suppression of expression of the target nucleic acid molecule is useful in improvement in the disease, this form of the nucleic acid molecule dimer of the present disclosure can be used for treating a disease associated with the expression of the target nucleic acid molecule while circumventing the induction of the cell response. When the nucleic acid molecule dimer of the present disclosure can increase the expression of the target nucleic acid molecule by RNAa or the like, this form of the nucleic acid molecule dimer of the present disclosure can be used for increasing the expression of the target nucleic acid molecule while circumventing the induction of the cell response. When the expression of the target nucleic acid molecule is related to a disease and when the increase in the expression of the target nucleic acid molecule is useful in improvement in the disease, this form of the nucleic acid molecule dimer of the present disclosure can be used for treating a disease associated with the expression of the target nucleic acid molecule while circumventing the induction of the cell response.

In some embodiments, the nucleic acid molecule dimer of the present disclosure, when administered to cells, can circumvent the enhanced expression of at least one gene selected from CCL5, CXCL10, IFNβ1, IL1β, IL6, IL10, IL13, TNF and CXCR4 genes. Specifically, the nucleic acid molecule dimer of the present disclosure, even if administered to cells, does not enhance the expression of the gene or enhances the expression of the gene to a low degree as compared with a nucleic acid molecule dimer that is similar thereto but has non-circular TNNA, for example, a nucleic acid molecule dimer that is similar thereto (e.g., having the same nucleotide sequence thereas) but has linear TNNA. In such embodiments, the nucleic acid molecule dimer of the present disclosure can be used for modulating the expression of the target nucleic acid molecule while circumventing the enhanced expression of at least one of the genes. When the expression of the target nucleic acid molecule is related to a disease, this form of the nucleic acid molecule dimer of the present disclosure can be used for treating a disease associated with the expression of the target nucleic acid molecule while circumventing the enhanced expression of at least one of the genes. When the nucleic acid molecule dimer of the present disclosure can suppress the expression of the target nucleic acid molecule by RNA silencing or the like, this form of the nucleic acid molecule dimer of the present disclosure can be used for suppressing the expression of the target nucleic acid molecule while circumventing the enhanced expression of at least one of the genes. When the expression of the target nucleic acid molecule is related to a disease and when the suppression of expression of the target nucleic acid molecule is useful in improvement in the disease, this form of the nucleic acid molecule dimer of the present disclosure can be used for treating a disease associated with the expression of the target nucleic acid molecule while circumventing the enhanced expression of at least one of the genes. When the nucleic acid molecule dimer of the present disclosure can increase the expression of the target nucleic acid molecule by RNAa or the like, this form of the nucleic acid molecule dimer of the present disclosure can be used for increasing the expression of the target nucleic acid molecule while circumventing the enhanced expression of at least one of the genes. When the expression of the target nucleic acid molecule is related to a disease and when the increase in the expression of the target nucleic acid molecule is useful in improvement in the disease, this form of the nucleic acid molecule dimer of the present disclosure can be used for treating a disease associated with the expression of the target nucleic acid molecule while circumventing the enhanced expression of at least one of the genes.

The nucleic acid molecule dimer of the present disclosure can be produced by a method comprising, for example, the steps of: circularizing linear TNNA; and annealing linear TCNA to the circularized TNNA, without limitations. A circular TNNA-containing nucleic acid molecule dimer which comprises circular TNNA obtained by circularizing linear TNNA is also referred to as a "circularized-TNNA nucleic acid molecule dimer". The step of circularizing linear TNNA can be achieved by an arbitrary known approach of circularizing a linear nucleic acid molecule. Examples of such an approach include, but are not limited to, enzymatic ligation using ligase or the like, and chemical ligation using BrCN, N-ethyl-N'-(3-dimethylaminopropyl) carbodiimide (also abbreviated to EDC or EDAC), imidazole, N-hydroxybenzotriazole, 1-mesitylenesulfonyl-3-nitro-1,2,4-triazole (MSNT), or the like.

The enzymatic ligation can be performed, for example, by allowing ligase (e.g., RNA ligase or DNA ligase according to the type of the nucleotides to be ligated) to act on linear TNNA having a phosphate group at the 5' end and a hydroxy group at the 3' end. The reaction temperature is preferably the optimum temperature for the enzyme or a temperature close thereto. The reaction time is not particularly limited and can be appropriately adjusted such that the desired degree of ligation is performed. The reaction time can be in the range of, for example, 6 hours to 36 hours or 12 hours to 24 hours. The ligation reaction may require ATP. Various types of ligase are commercially available, and the reaction conditions preferably follow manufacturer's instructions. If the desired degree of ligation is obtained, the ligase may be deactivated by heating or the like such that the ligase has no influence on subsequent reactions.

Various approaches are known for the chemical ligation. The ligation using BrCN can be performed by adding BrCN, imidazole and a divalent metal ion (e.g., $Mn^{2+}$, $Co^{2+}$, $Ni^{2+}$, $Cu^{2+}$, $Zn^{2+}$, $Mg^{2+}$, and $Fe^{2+}$) to linear TNNA having a phosphate group at the 5' end or the 3' end, followed by reaction for a predetermined time (e.g., Dolinnaya et al., Nucleic Acids Res. 1993; 21 (23): 5403-7; and Wang and Kool, Nucleic Acids Res. 1994; 22 (12): 2326-33). The ligation using EDC can be performed by incubating linear TNNA with EDC in a buffer solution (e.g., a buffer solution containing 2-morpholinoethanesulfonic acid and $MgCl_2$) (e.g., Dolinnaya et al., Nucleic Acids Res. 1988; 16 (9): 3721-38). The ligation using EDC employs linear TNNA having an amino group or a phosphate group at the 3' end and can thereby improve a reaction rate. The ligation using MSNT is described in, for example, Micura, Chem Eur J. 1999; 5 (7): 2077-82.

The circularized TNNA can be purified from the ligation reaction product and used in annealing to TCNA. An arbitrary known nucleic acid purification approach such as dialysis can be used in the purification. When the ligation reaction product contains unreacted linear TNNA, the linear TNNA may be eliminated by concentrating the circular TNNA through the degradation of the linear TNNA by the treatment of the reaction product with an enzyme, such as exonuclease, which selectively degrades a linear nucleic acid molecule, or by separating a nucleic acid molecule in the reaction product by electrophoresis (e.g., denaturing PAGE), and excising a band corresponding to the circular TNNA.

The annealing of the circular TNNA to linear TCNA can be performed by an arbitrary known approach. The annealing may be performed, for example, by heating TNNA and TCNA dissolved in an annealing buffer at approximately 70° C. to approximately 90° C. for approximately 1 minute to approximately 5 minutes, followed by incubation at approximately 37° C. for 0.5 to 2 hours, without limitations. Whether the annealing has been performed can be confirmed by, for example, electrophoresis (e.g., PAGE).

The linear TNNA is difficult to anneal directly (i.e., in a linear form) to TCNA, but can be designed such that its circularized form is easy to anneal to TCNA (e.g., such that a ligation site (i.e., the 5' end and the 3' end of the linear TNNA) when the linear TNNA is circularized does not agree with a nick or a gap to be formed by TCNA when the circularized TNNA is annealed to the TCNA). By such design of the linear TNNA, the sequence of the linear TNNA differs largely from a complementary sequence of TCNA and is thus less likely to form a linear nucleic acid molecule dimer by annealing to the TCNA, even if the reaction product is contaminated with uncircularized residual linear TNNA after circularization reaction of the linear TNNA. Therefore, the circular TNNA-containing nucleic acid molecule dimer of the present disclosure can be obtained at high purity, while off-target effects ascribable to linear TNNA can be circumvented. Thus, this approach is advantageous. This is particularly advantageous for enzymatically removing uncircularized TNNA with exonuclease or the like. Thus, the present disclosure provides a method for producing a circular TNNA-containing nucleic acid molecule dimer with high purity, comprising the step of providing linear TNNA that is difficult to anneal in a linear form to TCNA, but is easy to anneal in a circularized form to TCNA (e.g., linear TNNA designed such that a ligation site when the linear TNNA is circularized does not agree with a nick or a gap to be formed by TCNA when the circularized TNNA is annealed to the TCNA). The purity of the circular TNNA-containing nucleic acid molecule dimer obtained by this production method is higher than that of a circular TNNA-containing nucleic acid molecule dimer produced without the use of the linear TNNA described above. The present disclosure also relates to such a circular TNNA-containing nucleic acid molecule dimer with high purity. The purity described above refers to the ratio of the circular TNNA-containing nucleic acid molecule dimer to the final product in the step of producing the circular TNNA-containing nucleic acid molecule dimer, and can be calculated by dividing the number of moles of the circular TNNA-containing nucleic acid molecule dimer in the final product by the total number of moles of the final product, or by dividing the mass of the circular TNNA-containing nucleic acid molecule dimer in the final product by the total mass of the final product. The purity based on mass can be calculated, for example, on the basis of a peak ratio obtained by dividing the peak area of the circular TNNA-containing nucleic acid molecule dimer by the total peak area of the final product in the chromatogram of the final product (e.g., obtained by high-performance liquid chromatography (HPLC)).

In order to obtain the linear TNNA as described above, for example, the linear TNNA can be designed such that the number or ratio (e.g., the ratio to all nucleobases contained in TNNA or TCNA) of nucleobases contained in a continuous complementary region to be formed between the linear TNNA and the corresponding portion of TCNA is equal to or lower than a predetermined value. The ratio of the number of nucleobases contained in a continuous complementary region to be formed between the linear TNNA and the corresponding portion of TCNA to the total number of nucleobases contained in the TNNA can be, for example, approximately 75% or less, approximately 70% or less, approximately 65% or less, approximately 60% or less, approximately 55% or less, approximately 54% or less, or approximately 53% or less. Non-limiting examples of such a design approach will be shown below. In each sequence described below, Xn represents a nucleobase contained in TCNA, Yn represents a nucleobase contained in TNNA, and n represents the position of the nucleobase contained in TCNA from the 5' end. Yn is complementary to Xn with n representing the same number thereas (e.g., $Y_1$ is complementary to $X_1$).

(1) In the case where largest value of ratio of nucleobase pairs contained in continuous complementary region to be formed between linear TNNA and corresponding portion of TCNA is 100% of all nucleobases contained in TNNA TCNA:
5' $X_1X_2X_3X_4X_5X_6X_7X_8X_9X_{10}X_{11}X_{12}X_{13}X_{14}X_{15}X_{16}X_{17}X_{18}$ $X_{19}$ 3'

TNNA:
3' $Y_1Y_2Y_3Y_4Y_5Y_6Y_7Y_8Y_9Y_{10}Y_{11}Y_{12}Y_{13}Y_{14}Y_{15}Y_{16}$ 5'

In this example, all the nucleobases from positions 16 to 1 (in order from 5' toward 3') of TNNA are complementary to all the nucleobases in the corresponding portion (positions 1 to 16) of TCNA, and the number of nucleobases contained in the continuous complementary region to be formed between the linear TNNA and the corresponding portion of TCNA is 16. Thus, the ratio (%) of the number of these nucleobases to the total number of nucleobases contained in the TNNA is 16/16×100=100(%).

(2) In the case where largest value of ratio of nucleobase pairs contained in continuous complementary region to be formed between linear TNNA and corresponding portion of TCNA is 50% of all nucleobases contained in TNNA TCNA:
5' $X_1X_2X_3X_4X_5X_6X_7X_8X_9X_{10}X_{11}X_{12}X_{13}X_{14}X_{15}X_{16}X_{17}X_{18}$ $X_{19}$ 3'

TNNA:
3' $Y_9Y_{10}Y_{11}Y_{12}Y_{13}Y_{14}Y_{15}Y_{16}Y_1Y_2Y_3Y_4Y_5Y_6Y_7Y_8$ 5'

In this example, all the nucleobases from positions 8 to 1 ($Y_1Y_2Y_3Y_4Y_5Y_6Y_7Y_8$) of TNNA are complementary to all the nucleobases ($X_1X_2X_3X_4X_5X_6X_7X_8$) in the corresponding portion (positions 1 to 8) of TCNA, and all the nucleobases from positions 16 to 10 ($Y_9Y_{10}Y_{11}Y_{12}Y_{13}Y_{14}Y_{15}Y_{16}$) of the TNNA are complementary to all the nucleobases ($X_9X_{10}X_{11}X_{12}X_{13}X_{14}X_{15}X_{16}$) in the corresponding portion (positions 10 to 16) of the TCNA. Thus, the number of nucleobases contained in the continuous complementary region to be formed between the linear TNNA and the corresponding portion of TCNA is 8 at maximum, and the ratio (%) of the number of these nucleobases to the total number of nucleobases contained in the TNNA is 8/16×100=50(%). As for TNNA having 50% of this ratio, the largest value of the ratio of nucleobase pairs contained in the continuous complementary region to be formed with the corresponding portion of TCNA is lowest.

(3) In the case where largest value of ratio of nucleobase pairs contained in continuous complementary region to be formed between linear TNNA and corresponding portion of TCNA is 75% of all nucleobases contained in TNNA TCNA:
5' $X_1X_2X_3X_4X_5X_6X_7X_8X_9X_{10}X_{11}X_{12}X_{13}X_{14}X_{15}X_{16}X_{17}X_{18}$ $X_{19}$ 3'

TNNA:
3' $Y_5Y_6Y_7Y_8Y_9Y_{10}Y_{11}Y_{12}Y_{13}Y_{14}Y_{15}Y_{16}Y_1Y_2Y_3Y_4$ 5'

In this example, all the nucleobases from positions 4 to 1 ($Y_1Y_2Y_3Y_4$) of TNNA are complementary to all the nucleobases ($X_1X_2X_3X_4$) in the corresponding portion (positions 1 to 4) of TCNA, and all the nucleobases from positions 16 to 5 ($Y_5Y_6Y_7Y_8Y_9Y_{10}Y_{11}Y_{12}Y_{13}Y_{14}Y_{15}Y_{16}$) of the TNNA are complementary to all the nucleobases ($X_5X_6X_7X_8X_9X_{10}X_{11}X_{12}X_{13}X_{14}X_{15}X_{16}$) in the corresponding portion (positions 5 to 16) of the TCNA. Thus, the number of nucleobases contained in the continuous complementary region to be formed between the linear TNNA and the corresponding portion of TCNA is 12 at maximum, and the ratio (%) of the number of these nucleobases to the total number of nucleobases contained in the TNNA is 12/16×100=75(%).

Figure 2:
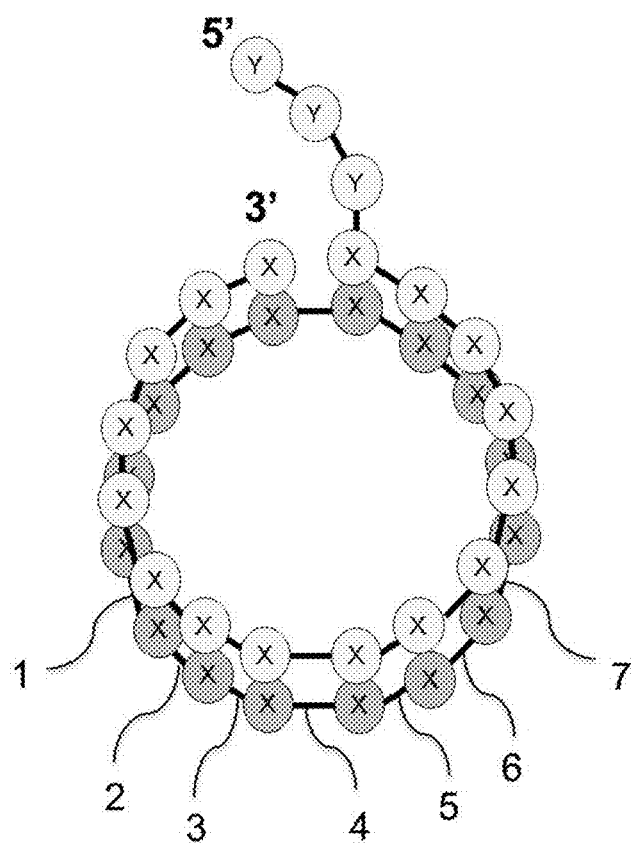
FIG. 2 is a diagram showing examples of ligation sites of TNNA to be set for the production of the nucleic acid molecule dimer of the present disclosure.

Another example of the approach of obtaining the linear TNNA as described above includes the design of the linear TNNA such that a ligation site (i.e., the 5' end and the 3' end of the linear TNNA) when the linear TNNA is circularized is located at a position different from that of a nick or a gap to be formed by TCNA when the circularized TNNA is annealed to the TCNA. It is preferred to design the linear TNNA such that the ligation site is positioned distant from the nick or the gap, and it is particularly preferred to design the linear TNNA such that the ligation site is located on a side opposite to the nick or the gap, or at a site near the opposite side. In this context, the opposite side means, for example, a position on TNNA point-symmetric with the midpoint of the nick or the gap with respect to the center of a circle when all monomers constituting the TNNA are evenly arranged on the circumference of the circle. FIG. 2 shows a preferred non-limiting example of the ligation site. In the nucleic acid molecule dimer shown in FIG. 2, TCNA has a nick and a 5' overhang, and the position on TNNA on a side opposite to the nick is 4. The site near the side opposite to the nick can be, for example, 1 to 3 and 5 to 7, 2 to 3 and 5 to 6, or 3 and 5. When an odd number of nucleotides constitutes TNNA, the position on TNNA on a side opposite to the nick is the 3' side or the 5' side of a nucleotide positioned on a side just opposite to the nick.

The nucleic acid molecule dimer of the present disclosure may be delivered or administered together with an arbitrary known delivery carrier having an effect of assisting in, promoting or facilitating delivery to a site of action, or may be delivered or administered directly without such a delivery carrier. A viral vector or a non-viral vector can be used as the delivery carrier. Examples of the non-viral vector include, but are not limited to, carriers in a particle form such as polymer particles, lipid particles, and inorganic particles. Nanoparticles having a nano level of size can be used as the particles. Examples of the polymer particles include, but are not limited to, those containing polymers such as cationic polymers, polyamidoamine (PAMAM), chitosan, cyclodextrin, poly(lactic-co-glycolic acid) (PLGA), poly(lactic-co-caprolactonic acid) (PLCA), poly(β amino ester), and atelocollagen. Examples of the cationic polymer include polylysine (e.g., poly-L-lysine (PLL)), polyethylenimine (PEI), and their derivatives. Examples of the polyethylenimine derivative include polyethylenimine-polyethylene glycol copolymers (PEI-PEG), polyethylenimine-polyethylene glycol-N-acetylgalactosamine (PEI-PEG-GAL), polyethylenimine-polyethylene glycol-tri-N-acetylgalactosamine (PEI-PEG-triGAL), and graft PEI, for example, galactose PEI, cholesterol PEI, and antibody-derivatized PEI. A polymer containing amine is capable of exerting a proton sponge effect advantageous for endosomal escape when incorporated into the endosome.

The lipid particles include liposomes, non-liposomal lipid particles, and the like. The liposome is a vesicle having a lumen surrounded by a lipid bilayer. The non-liposomal lipid particles are lipid particles having no such structure. The lipid particles may contain a cationic lipid, an ionizable lipid, a helper lipid, or the like. The cationic lipid is particularly useful for introducing a negatively charged nucleic acid molecule or the like into cells. Non-limiting examples of the cationic lipid include N-(α-trimethylammonioacetyl)-didodecyl-D-glutamate chloride (TMAG), N,N', N'',N'''-tetramethyl-N,N',N'',N'''-tetrapalmitylspermine (TMTPS), 2,3-dioleyloxy-N-[2(sperminecarboxamido)ethyl]-N,N-dimethyl-1-propanaminium trifluoroacetate (DOSPA), N-[1-(2,3-dioleyloxy)propyl]-N,N,N-trimethylammonium chloride (DOTMA), dioctadecyl dimethylammonium chloride (DODAC), didodecyl ammonium bromide (DDAB), 1,2-dioleyloxy-3-trimethylammoniopropane (DO-TAP), 3β-[N—(N',N'-dimethylaminoethane)carbamoyl] cholesterol (DC-Chol), 1,2-dimyristoyloxypropyl-3-dimethylhydroxyethylammonium bromide (DMRIE), and O,O'-ditetradecanoyl-N-(α-trimethylammonioacetyl) diethanolamine chloride (DC-6-14). Examples of other useful cationic lipids are also described in, for example, WO 2012/170952.

Examples of the ionizable lipid include ionizable cationic lipids. The ionizable cationic lipid has a property of being nonionic at pH equal to or higher than PKa but being cationic at pH lower than PKa. The ionizable lipid may have tertiary amine. Such an ionizable lipid containing amine is capable of exerting a proton sponge effect advantageous for endosomal escape when incorporated into the endosome. In some embodiments, the PKa of the ionizable cationic lipid can be, for example, 7.0 or higher, 7.5 or higher, 7.6 or higher, 7.8 or higher, or 8.0 or higher. Non-limiting examples of the ionizable lipid include DLinDAP, DLinDMA, DLinKDMA, and DLinKC2-DMA. Examples of other useful ionizable cationic lipids are also described in, for example, WO 2013/185116.

The helper lipid is a lipid that contributes to the stabilization of lipid particles, etc. The helper lipid may be neutral in terms of charge. Non-limiting examples of the helper lipid include cholesterol, dioleoylphosphatidylethanolamine (DOPE), oleoylpalmitoyl-phosphatidylethanolamine (POPE), diphytanoylphosphatidylethanolamine (DPhPE), distearoylphosphatidylethanolamine (DSPE), dipalmitoylphosphatidylethanolamine (DPPE), dimyristoylphosphatidylethanolamine (DMPE), and PEG lipid.

Examples of the inorganic particles include gold nanoparticles, quantum dots, silica nanoparticles, iron oxide nanoparticles (e.g., superparamagnetic iron oxide nanoparticles (SPION)), nanotubes (e.g., carbon nanotubes (CNT)), nanodiamond, and fullerene.

Various modifications can be added to the particle carrier described above. Examples thereof include stealthing with PEG, targeting with a targeting ligand, and modification with a cell penetrating peptide (CPP).

The nucleic acid molecule dimer of the present disclosure may be conjugated with a functional moiety such as the polymer described above, a targeting ligand, or CPP by binding. Such a conjugate permits formulation of the nucleic acid molecule dimer of the present disclosure without the use of the carrier described above. The functional moiety may be bound to any of TCNA and TNNA and is preferably bound to TNNA which is considered to have no direct effect on the target nucleic acid molecule. The functional moiety can be bound to an arbitrary portion of the TNNA. In a particular embodiment, the functional moiety is bound to a portion of TNNA where TCNA forms a nick or a gap. In other embodiments, the functional moiety is bound to a portion of TNNA distant from the location of a nick or a gap formed by TCNA, for example, a portion of TNNA on a side opposite to the nick or the gap.

The nucleic acid molecule dimer of the present disclosure can be systemically administered or locally administered ex vivo or in vivo to a tissue concerned via skin application, transdermal application or injection (intravenous injection, intradermal injection, subcutaneous injection, intramuscular injection, intraarterial injection, drip injection, etc.). The nucleic acid molecule dimer of the present disclosure can be administered by pulmonary delivery, for example, the inhalation of an aerosol or a spray-dried preparation to be administered with an inhalation apparatus or a nebulizer which brings about rapid local incorporation of a nucleic acid molecule to a lung tissue concerned. The nucleic acid molecule dimer of the present disclosure can also be administered to the central nervous system (CNS) or the peripheral nervous system (PNS). The delivery of the nucleic acid molecule to CNS can be performed by, for example, subarachnoidal and intracerebroventricular administration, transplantation of a catheter and a pump, direct injection or perfusion to an injury site or a lesion site, injection to the cerebral arterial system, or chemical or osmotic opening of the blood-brain barrier, without limitations.

The nucleic acid molecule dimer of the present disclosure can be delivered through a delivery system suitable for a purpose. The delivery system may include, for example, aqueous and non-aqueous gels, creams, double emulsions, microemulsions, liposomes, ointments, aqueous and non-aqueous solutions, lotions, aerosols, hydrocarbon bases and powders and can include excipients, for example, solubilizers, penetration enhancers (e.g., fatty acids, fatty acid esters, aliphatic alcohols and amino acids) and hydrophilic polymers (e.g., polycarbophil and polyvinylpyrrolidone). In one embodiment, the pharmaceutically acceptable carrier is a liposome or a transdermal delivery enhancer.

The delivery system may include patches, tablets, suppositories, pessaries, gels and creams and can include excipients, for example, solubilizers and enhancers (e.g., propylene glycol, bile salt and amino acids) and other vehicles (e.g., polyethylene glycol, fatty acid esters and derivatives, and hydrophilic polymers, for example, hydroxypropylmethylcellulose and hyaluronic acid).

Approaches and systems useful in the delivery of the nucleic acid molecule dimer of the present disclosure are described in, for example, Rettig and Behlke, Mol Ther. 2012; 20 (3): 483-512, Kraft et al., J Pharm Sci. 2014; 103 (1): 29-52, Hong and Nam, Theranostics. 2014; 4 (12): 1211-32, and Kaczmarek et al., Genome Med. 2017; 9 (1): 60.

In some embodiments, the present disclosure relates to a composition comprising the nucleic acid molecule dimer of the present disclosure (hereinafter, also referred to as the composition of the present disclosure). The composition of the present disclosure may comprise one nucleic acid molecule dimer or two or more different nucleic acid molecule dimers. When the composition of the present disclosure comprises two or more different nucleic acid molecule dimers, the nucleic acid molecule dimers may be directed to different target nucleic acid molecules or may be directed to different sequences (regions) of one target nucleic acid molecule. The composition of the present disclosure may comprise the arbitrary carrier mentioned above, a diluent, a delivery vehicle, a delivery system, and the like, in addition to the nucleic acid molecule dimer of the present disclosure. The composition of the present disclosure can be used in the treatment of a disease associated with a target nucleic acid molecule. Thus, the composition of the present disclosure may serve as a pharmaceutical composition for the treatment of a disease associated with a target nucleic acid molecule (hereinafter, also referred to as the pharmaceutical composition of the present disclosure). The pharmaceutical composition of the present disclosure may comprise one or two or more pharmaceutically acceptable additives (e.g., surfactants, carriers, diluents, and excipients). The pharmaceutically acceptable additives are well known in the medical field and described in, for example, Remington's Pharmaceutical Sciences, 18th Ed., Mack Publishing Co., Easton, Pa. (1990), which is incorporated herein by reference in its entirety.

In some embodiments, the pharmaceutical composition of the present disclosure can be used for the treatment of a disease associated with the expression of the target nucleic acid molecule, as in the nucleic acid molecule dimer of the present disclosure. In a particular embodiment, the pharmaceutical composition of the present disclosure can be used for treating a disease associated with the expression of the target nucleic acid molecule while circumventing at least one of off-target effects ascribable to TNNA, the phosphorylation of PKR, the activation of the TLR3 pathway and the induction of sequence-non-specific cell response (e.g., natural immunity) by a nucleic acid molecule. Also, the pharmaceutical composition of the present disclosure can be used for treating a disease associated with the expression of the target nucleic acid molecule while circumventing the enhanced expression of at least one gene selected from CCL5, CXCL10, IFNβ1, IL1β, IL6, IL10, IL13, TNF and CXCR4 genes.

In the present disclosure, the "treatment" includes every type of medically acceptable prophylactic and/or therapeutic intervention aimed at cure, transient remission or prevention, etc. of a disease. The "treatment" includes medically acceptable intervention for various purposes including, for example, the delay or arrest of progression of a disease associated with a target nucleic acid molecule, the regression or disappearance of a lesion, the prevention of onset of the disease or the prevention of recurrence of the disease. Thus, the nucleic acid molecule dimer and the pharmaceutical composition include a pharmaceutical composition for the therapy of a disease associated with a target nucleic acid molecule, and a pharmaceutical composition for the prophylaxis of a disease associated with a target nucleic acid molecule.

The nucleic acid molecule dimer or the pharmaceutical composition of the present disclosure may be administered through various routes including both oral and parenteral routes, for example, but not limited to, oral, buccal, mouth, intravenous, intramuscular, subcutaneous, intradermal, local, rectal, intraarterial, intraportal, intraventricular, transmucosal, transdermal, intranasal, intraperitoneal, intratracheal, intrapulmonary and intrauterine routes, and may be formulated into a dosage form suitable for each administration route. Arbitrary ones known in the art can be appropriately adopted to such a dosage form and a formulation method (see e.g., Remington's Pharmaceutical Sciences, 18th Ed., Mack Publishing Co., Easton, Pa. (1990)).

Examples of the dosage form suitable for oral administration include, but are not limited to, powders, granules, tablets, capsules, solutions, suspensions, emulsions, gels, and syrups. Examples of the dosage form suitable for parenteral administration include injections such as solution-type injections, suspension-type injections, emulsion-type injection, and injections to be prepared in use. The preparation for parenteral administration can be in the form of an aqueous or non-aqueous isotonic sterile solution or suspension.

The composition according to the present disclosure may be supplied in any form and may be provided in a form capable of being prepared in use, for example, a form capable of being prepared by a physician and/or a pharmacist, a nurse, or other paramedical crews, etc. in or near medical practice, from the viewpoint of preservation stability. In this case, the composition is provided in one or two or more containers comprising at least one component essential therefor, and prepared before use, for example, within 24 hours before use, preferably within 3 hours before use, more preferably immediately before use. For the preparation, a reagent, a solvent, dispensing equipment, and the like usually available in a preparation location can be appropriately used.

In further aspects, the present disclosure relates to a kit or a pack for preparing the composition and/or for treating a disease associated with a target nucleic acid molecule, comprising the composition according to the present disclosure or a component thereof, and the composition or a necessary component thereof that is provided in the form of such a kit or a pack. Each component of the composition contained in this kit or pack is as described above about the composition. The present kit may further comprise instructions as to a method for preparing or using (e.g., administering) the composition, for example, instruction manuals, and a medium, for example, a flexible disc, CD, DVD, a Blu-ray disc, a memory card, or a USB memory, in which information on the use method is recorded, in addition to those described above. Also, the kit or the pack may comprise all components for completing the composition or may not necessarily comprise all the components. Thus, the kit or the pack may not comprise a reagent or a solvent usually available in medical practice, an experimental facility, etc., for example, sterile water, saline, or a glucose solution.

In an alternative aspect, the present disclosure relates to a method for treating a disease associated with a target nucleic acid molecule, the method comprising the step of administering an effective amount of the nucleic acid molecule dimer or the pharmaceutical composition according to the present disclosure comprising a drug for treating the disease to a subject in need thereof (hereinafter, also referred to as the "treatment method of the present disclosure"). In this context, the effective amount is, for example, an amount in which the onset and recurrence of the disease are prevented, or the disease is cured.

In the treatment method, the specific dose of the nucleic acid molecule dimer or the pharmaceutical composition to be administered to the subject may be determined in consideration of various conditions as to the subject in need of the administration, for example, the type of the target, the purpose of the method, a therapeutic regimen, the type of the disease, the severity of symptoms, the general health state, age, and body weight of the subject, the sex of the subject, diets, the timing and frequency of administration, a concurrent drug, responsiveness to therapy, and compliance with therapy. The total daily dose of the pharmaceutical composition is not limited and may be, for example, approximately 1 µg/kg to approximately 1000 mg/kg body weight, approximately 10 µg/kg to approximately 100 mg/kg body weight, or approximately 100 µg/kg to approximately 10 mg/kg body weight, in terms of the amount of the nucleic acid molecule dimer. Alternatively, the dose may be calculated on the basis of the surface area of a patient.

The administration route includes various routes including both oral and parenteral routes, for example, oral, buccal, mouth, intravenous, intramuscular, subcutaneous, intradermal, local, rectal, intraarterial, intraportal, intraventricular, transmucosal, transdermal, intranasal, intraperitoneal, intratracheal, intrapulmonary and intrauterine routes.

The frequency of administration differs depending on the properties of the preparation or the composition used or the conditions of the subject as described above and may be, for example, plural times per day (i.e., 2, 3, 4 or 5 or more times per day), once a day, every few days (i.e., every 2, 3, 4, 5, 6, or 7 days), several times a week (e.g., 2, 3, or 4 times a week), every week, or every few weeks (i.e., every 2, 3, or 4 weeks).

In the present disclosure, the term "subject" means an arbitrary organism individual, preferably animal, more preferably mammalian, further preferably human individual. The subject may be healthy (e.g., have no particular or arbitrary disease) or may be affected by some disease. When the treatment of a disease associated with a target nucleic acid molecule is intended, for example, the subject typically means a subject affected by the disease or having a risk of being affected by the disease.

In an alternative aspect, the present disclosure relates to a method for modulating the expression of a target nucleic acid molecule, the method comprising the step of administering an effective amount of the nucleic acid molecule dimer or the pharmaceutical composition according to the present disclosure to a cell containing the target nucleic acid molecule (hereinafter, also referred to as the "expression modulation method of the present disclosure"). In this context, the effective amount is, for example, an amount in which the expression of the target nucleic acid molecule can be detectably modulated. The expression of the target nucleic acid molecule involved in protein production can be detected by a known protein detection approach, for example, an immunoprecipitation method using an antibody, EIA (enzyme immunoassay) (e.g., ELISA (enzyme-linked immunosorbent assay)), RIA (radioimmunoassay) (e.g., IRMA (immunoradiometric assay), RAST (radioallergosorbent test), and RIST (radioimmunosorbent test)), Western blotting, an immunohistochemical method, an immunocytochemical method, or flow cytometry, without limitations. The expression of the target nucleic acid molecule involved in nucleic acid molecule production can be detected by a known nucleic acid molecule detection approach, for example, various hybridization methods, Northern blotting, Southern blotting, or various PCR methods using a nucleic acid specifically hybridizing to the nucleic acid molecule or a unique fragment thereof, without limitations. When the expression of the target nucleic acid molecule is the expression of biological activity, the biological activity can be detected by an arbitrary known detection approach. The expression modulation method of the present disclosure can be performed in vitro, ex vivo or in vivo. The administration of the nucleic acid molecule dimer or the pharmaceutical composition to the cell can be performed by an arbitrary known approach, for example, can be performed in vivo through various routes including both the oral and parenteral routes as described above about the treatment method of the present disclosure, or can be performed in vitro or ex vivo by the addition of the nucleic acid molecule dimer or the pharmaceutical composition to a medium (e.g., a culture medium) containing the cell.

EXAMPLES

Hereinafter, the present invention will be described in more detail with reference to Examples. However, the scope of the present invention is not limited by these examples.

Example 1: Production of Circular Nucleic Acid Molecule-Containing Nucleic Acid Molecule Dimer (CNA-NAD)

CNA-NAD was produced by circularizing a linear target-non-complementary nucleic acid molecule (target non-complementary nucleic acid: TNNA), and annealing thereto a linear target complementary nucleic acid molecule (target complementary nucleic acid: TCNA).

(1) Sequence Used

TNNA used had the following sequence.

TABLE 1

Sequence of TNNA

| Name | Sequence | SEQ ID NO |
|---|---|---|
| TN-1 | 5'-P-GAGCUGCUCCAUUAAC-3' | 1 |
| TN-2 | 5'-P-CUGCUUAAUUAACGAG-3' | 2 |
| TN-3 | 5'-P-GAAUAUGACCAAAGUC-3' | 3 |
| TN-4 | 5'-P-CUGCUUAACAUUAACGAG-3' | 4 |
| TN-5 | 5'-P-CUGCUUAACCAUUAACGAG-3' | 5 |
| TN-6 | 5'-P-GAAUAUGACAACCAAAGUC-3' | 6 |
| TN-7 | 5'-P-CUGCUUAAAACCAUUAACGAG-3' | 7 |
| TN-8 | 5'-P-CUGCUUAACCAACCAUUAACGAG-3' | 8 |
| TN-9 | 5'-P-CUGCUUAAGCCCAACCAUUAACGAG-3' | 9 |
| TN-10 | 5'-P-UUCAAGGACCAUCUUC-3' | 10 |
| TN-11 | 5'-P-UCUUCUUCGCGCACCA-3' | 11 |
| TN-12 | 5'-CCAUUAACGAGCUGCU-3' | 12 |
| TN-13 | 5'-CUGCUUAAUUAACGAG-3' | 13 |
| TN-14 | 5'-UUAACGAGCUGCUUAA-3' | 14 |
| TN-15 | 5'-CCAAAGUCGAAUAUGA-3' | 15 |
| TN-16 | 5'-CCAUUAACGAGCUGCUUAA-3' | 16 |
| TN-17 | 5'-CUGCUUAACCAUUAACGAG-3' | 17 |
| TN-18 | 5'-CAACCAAAGUCGAAUAUGA-3' | 18 |
| TN-19 | 5'-CCAUUAACGAGCUGCUUAAdTdT-3' | 19 |
| TN-20 | 5'-CAACCAAAGUCGAAUAUGAdTdT-3' | 20 |
| TN-21 | 5'-CCAUCUUCUUCAAGGA-3' | 21 |
| TN-22 | 5'-GCGCACCAUCUUCUUC-3' | 22 |

TABLE 1-continued

Sequence of TNNA

| Name | Sequence | SEQ ID NO |
|---|---|---|
| TN-23 | 5'-GCACCAUCUUCUUCAAGGA-3' | 23 |
| TN-24 | 5'-GGAGCGCACCAUCUUCUUC-3' | 24 |

TCNA used had the following sequence.

TABLE 2

Sequence of TCNA

| Name | Sequence | SEQ ID NO |
|---|---|---|
| TC-1 | 5'-UUAAGCAGCUCGUUAAUGG-3' | 25 |
| TC-2 | 5'-UCAUAUUCGACUUUGGUUG-3' | 26 |
| TC-3 | 5'-UUAAGCAGCUCGUUAAUGGUU-3' | 27 |
| TC-4 | 5'-UUAAGCAGCUCGUUAAUGGdTdT-3' | 28 |
| TC-5 | 5'-UCAUAUUCGACUUUGGUUGdTdT-3' | 29 |
| TC-6 | 5'-UUAAGC + AGCUCGUUAAUGG-3' | 30 |
| TC-7 | 5'-UUAAGC + AGCUCGUUA + AUGG-3' | 31 |
| TC-8 | 5'-P-UUAAGCAGCUCGUUAAUGG-3' | 32 |
| TC-9 | 5'-UCCUUGAAGAAGAUGGUGC-3' | 33 |
| TC-10 | 5'-GAAGAAGAUGGUGCGCUCC-3' | 34 |
| TC-11 | 5'-UUAAGCAGCUCGUUAA-3' | 35 |

In the tables, A, C, G and U represent RNA, dA, dC, dG and dT represent DNA, P represents a phosphate group, and + represents LNA.

(2) Circularization of TNNA

Figure 3:
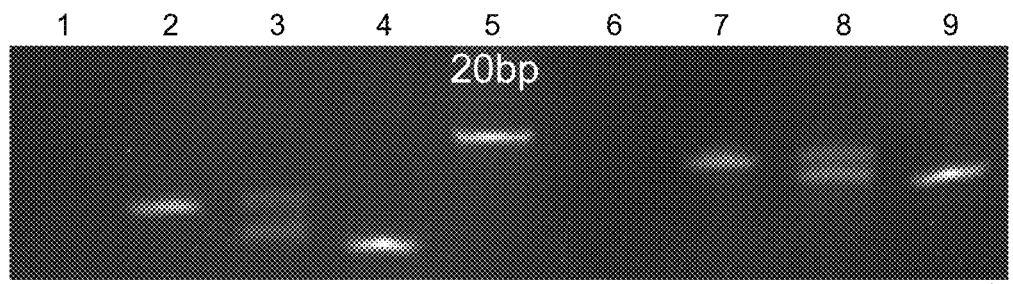
FIG. 3 is a diagram showing results of confirming by denaturing PAGE whether TNNA was circularized. Lanes 2 and 7 depict 5' phosphorylated linear TNNA (TN-2 and TN-5). Lanes 1 and 6 depict 5' phosphorylated linear TNNA treated with RNase R. Lanes 3 and 8 depict 5' phosphorylated linear TNNA circularized with T4 RNA Ligase 1. Lanes 4 and 9 depict a circularization reaction product treated with RNase R. Lane 5 depicts a molecular weight marker. TNNA shown in lanes 1 to 4 is 16 mer, and TNNA shown in lanes 6 to 9 is 19 mer. Of two bands observed in lanes 3 and 8, the upper band depicts uncircularized linear TNNA, and the lower band depicts circularized TNNA.

RNA ligase (T4 RNA Ligase 1, New England Biolabs Inc.) and linear TNNA having a phosphate group at the 5' end and a hydroxy group at the 3' end were reacted at 37° C. for 16 hours in the presence of ATP according to manufacturer's instructions to ligate the 5' end and the 3' end of the TNNA. After completion of the reaction, the reaction product was incubated at 65° C. for 15 minutes to deactivate the RNA ligase. The reaction product was applied to 20% T denaturing polyacrylamide/urea gel and electrophoresed at 250 V for 90 minutes. The gel was stained with 0.5 µg/mL ethidium bromide for 15 minutes, and a band was detected with UV. DynaMarker® Small RNA II Easy Load (BioDynamics Laboratory, Inc.) was used as a ladder marker. The results of electrophoresis using TN-2 and TN-5 as the TNNA are shown in FIG. 3. The TNNA before ligation was used as a non-circularized control, and TN-2 and TN-5 circularized as described above and then treated with RNase R (Epicentre Technologies Corp.) in order to concentrate the circularized nucleic acid molecule were each used as a circularized control. As is evident from FIG. 3, TNNA having a phosphate group at the 5' end (TN-2 and TN-5) was circularized. The band of the circularized nucleic acid molecule was excised, and after grinding of the gel, the circularized nucleic acid molecule was eluted into water at 37° C. for 4 hours or longer, coprecipitated with Dr. GenTLE® Precipitation Carrier (Takara Bio Inc.), and purified. The resultant was dissolved in RNase-free water and used as circular TNNA (CTNNA) in subsequent experiments.

(3) Annealing

Figure 4:
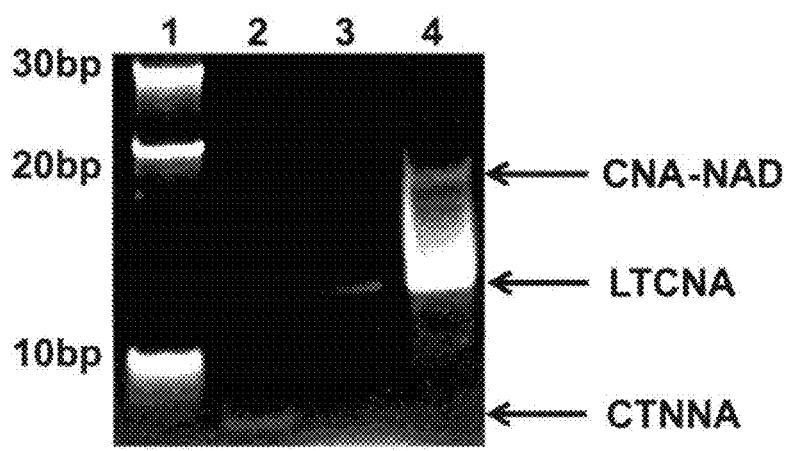
FIG. 4 is a diagram showing results of confirming by native PAGE whether circular TNNA (CTNNA) and linear TCNA (LTCNA) were annealed. Lane 1 depicts a molecular weight marker. Lane 2 depicts circular TNNA alone. Lane 3 depicts linear TCNA alone. Lane 4 depicts circular TNNA and linear TCNA annealed to each other. Of two bands observed in lane 4, the upper band depicts a circular nucleic acid molecule-containing nucleic acid molecule dimer (CNA-NAD) in which circular TNNA and linear TCNA were annealed.

6 µL of the CTNNA-containing nucleic acid molecule solution obtained in the preceding section (2), 6 µL of each nucleic acid molecule solution containing linear TCNA (LTCNA) with the same molar concentration as that of CTNNA dissolved in RNase-free water, and 3 µL of an annealing buffer Tris-EDTA buffer (10 mM Tris-HCl, 50 mM NaCl, and 1 mM EDTA) were mixed and reacted at 80° C. for 5 minutes and subsequently at 37° C. for 1 hour. In order to confirm the annealing, the reaction product was analyzed by native PAGE. The reaction product was applied to 20% polyacrylamide gel and electrophoresed at 200 V for 70 minutes. The gel was stained with 0.5 µg/mL ethidium bromide for 15 minutes, and a band was detected with UV. DynaMarker® Small RNA II Easy Load (BioDynamics Laboratory, Inc.) was used as a ladder marker. The results of electrophoresis using TN-2 as the TNNA and TC-1 as the TCNA are shown in FIG. 4. From the results shown in this drawing, it was confirmed that the CTNNA and the LTCNA were annealed.

CNA-NAD described below was produced by the approach described above. In the following table, "Length (TN/TC)" represents "length of TNNA/length of TCNA".

TABLE 3

Production Example of circular TNNA-containing nucleic acid molecule dimer

| Name | TNNA | TCNA | Target gene | Length (TN/TC) | Structure |
|---|---|---|---|---|---|
| CL-1 | TN-1 | TC-1 | PLK 1 | 16/19 | 5' end overhang on TCNA |
| CL-2 | TN-2 | TC-1 | PLK 1 | 16/19 | 3' end overhang on TCNA |
| CL-3 | TN-3 | TC-2 | PLK 1 | 16/19 | 3' end overhang on TCNA |
| CL-4 | TN-5 | TC-4 | PLK 1 | 19/21 | 3' end overhang on TCNA |
| CL-5 | TN-5 | TC-1 | PLK 1 | 19/19 | Nick on TCNA |
| CL-6 | TN-6 | TC-2 | PLK 1 | 19/19 | Nick on TCNA |
| CL-7 | TN-4 | TC-1 | PLK 1 | 18/19 | 3' end overhang on TCNA |
| CL-8 | TN-7 | TC-1 | PLK 1 | 21/19 | Gap on TCNA |
| CL-9 | TN-8 | TC-1 | PLK 1 | 23/19 | Gap on TCNA |
| CL-10 | TN-9 | TC-1 | PLK 1 | 25/19 | Gap on TCNA |
| CL-11 | TN-2 | TC-4 | PLK 1 | 16/21 | 3' end overhang on TCNA |
| CL-12 | TN-4 | TC-4 | PLK 1 | 18/21 | 3' end overhang on TCNA |
| CL-13 | TN-7 | TC-4 | PLK 1 | 21/21 | 3' end overhang + gap on TCNA |
| CL-14 | TN-8 | TC-4 | PLK 1 | 23/21 | 3' end overhang + gap on TCNA |

TABLE 3-continued

Production Example of circular TNNA-containing nucleic acid molecule dimer

| Name | TNNA | TCNA | Target gene | Length (TN/TC) | Structure |
|---|---|---|---|---|---|
| CL-15 | TN-9 | TC-4 | PLK 1 | 25/21 | 3' end overhang + gap on TCNA |
| CL-16 | TN-2 | TC-3 | PLK 1 | 16/21 | 3' end overhang on TCNA |
| CL-17 | TN-4 | TC-3 | PLK 1 | 18/21 | 3' end overhang on TCNA |
| CL-18 | TN-5 | TC-3 | PLK 1 | 19/21 | 3' end overhang on TCNA |
| CL-19 | TN-7 | TC-3 | PLK 1 | 21/21 | Nick on TCNA |
| CL-20 | TN-8 | TC-3 | PLK 1 | 23/21 | Gap on TCNA |
| CL-21 | TN-9 | TC-3 | PLK 1 | 25/21 | Gap on TCNA |
| CL-22 | TN-2 | TC-6 | PLK 1 | 16/19 | 3' end overhang on TCNA |
| CL-23 | TN-2 | TC-7 | PLK 1 | 16/19 | 3' end overhang on TCNA |
| CL-24 | TN-10 | TC-9 | GFP | 16/19 | 3' end overhang on TCNA |
| CL-25 | TN-11 | TC-10 | GFP | 16/19 | 3' end overhang on TCNA |

The following CNA-NAD was produced in the same way as above except that TCNA was circularized instead of TNNA.

TABLE 4

Production Example of circular TCNA-containing nucleic acid molecule dimer

| Name | TNNA | TCNA | Target gene | Length (TN/TC) | Structure |
|---|---|---|---|---|---|
| LC-1 | TN-17 | TC-8 | PLK 1 | 19/19 | Nick on TNNA |

The following nucleic acid molecule dimer was produced by annealing linear TNNA and linear TCNA as described above in the section (3) without circularizing both TNNA and TCNA.

TABLE 5

Production Example of TNNA/TCNA non-circularized nucleic acid molecule dimer

| Name | TNNA | TCNA | Target gene | Length (TN/TC) | Structure |
|---|---|---|---|---|---|
| LL-1 | TN-13 | TC-11 | PLK 1 | 16/16 | Circular, nick on TNNA and TCNA |
| LL-2 | TN-17 | TC-1 | PLK 1 | 19/19 | Circular, nick on TNNA and TCNA |
| LL-3 | TN-13 | TC-1 | PLK 1 | 16/19 | Circular, gap on TNN, nick on TCNA |
| LL-4 | TN-17 | TC-4 | PLK 1 | 19/21 | Circular, gap on TNNA, nick on TCNA |
| LL-5 | TN-12 | TC-1 | PLK 1 | 16/19 | Linear, 3' end overhang on AS strand |
| LL-6 | TN-16 | TC-1 | PLK1 | 19/19 | Linear, blunt end |
| LL-7 | TN-12 | TC-4 | PLK1 | 16/21 | Linear, 3' end overhang on TCNA |
| LL-8 | TN-16 | TC-4 | PLK1 | 19/21 | Linear, 3' end overhang on TCNA |
| LL-9 | TN-19 | TC-4 | PLK1 | 21/21 | Linear, 3' end overhang on TCNA |
| LL-10 | TN-12 | TC-3 | PLK1 | 16/21 | Linear, 3' end overhang on TCNA |
| LL-11 | TN-16 | TC-3 | PLK1 | 19/21 | Linear, 3' end overhang on TCNA |
| LL-12 | TN-12 | TC-6 | PLK1 | 16/19 | Linear, 3' end overhang on TCNA |
| LL-13 | TN-12 | TC-7 | PLK1 | 16/19 | Linear, 3' end overhang on TCNA |
| LL-14 | TN-21 | TC-9 | GFP | 16/19 | Linear, 3' end overhang on TCNA |
| LL-15 | TN-23 | TC-9 | GFP | 19/19 | Linear, blunt end |
| LL-16 | TN-22 | TC-10 | GFP | 16/19 | Linear, 3' end overhang on TCNA |
| LL-17 | TN-24 | TC-10 | GFP | 19/19 | Linear, blunt end |
| LL-18 | TN-15 | TC-2 | PLK 1 | 16/19 | Linear, 3' end overhang on TCNA |
| LL-19 | TN-18 | TC-2 | PLK 1 | 19/19 | Linear, blunt end |
| LL-20 | TN-20 | TC-5 | PLK 1 | 21/21 | Linear, 3' end overhang on S/TCNA |

Example 2: Knockdown Effects of Circular TNNA-Containing Nucleic Acid Molecule Dimer—(1)

A549 cells were inoculated at a density of $0.1 \times 10^5$ cells/well to a 24-well plate and incubated at 37° C. under 5% $CO_2$ in Dulbecco's modified Eagle's medium (DMEM, Sigma-Aldrich Co. LLC) containing 10% FBS. On the next day, a sample containing Lipofectamine RNAiMAX Transfection Reagent (Thermo Fisher Scientific Inc.) and each nucleic acid molecule in Opti-MEM (Sigma-Aldrich Co. LLC) medium was added to the A549 cell cultures according to manufacturer's protocol such that the final concentration of the nucleic acid molecule was 10 nM, followed by transfection for 5 hours. After the transfection, the medium was replaced with DMEM medium containing 10% FBS. 24 hours after the start of the transfection, RNA was extracted using RNeasy Mini Kit (Qiagen N.V.) and subjected to reverse transcription reaction using SuperScript VILO Master Mix (Thermo Fisher Scientific Inc.). Then, real-time PCR was performed using SYBR Green PCR Master Mix (Thermo Fisher Scientific Inc.) to measure the expression level of PLK1. The results are shown in the table below. In the table, the residual rate of mRNA was indicated by ratio (%) when the residual rate of mRNA in an untreated group (NT) was defined as 100%. A mRNA residual rate of 30% or less at a RNA concentration of 10 nM was determined as pass (represented by circle).

TABLE 6 mRNA residual rate of various nucleic acid molecule dimers mRNA residual rate (%, NT = 100%)

| Name | Exp. 1 | Exp. 2 | Exp. 3 | Exp. 4 | Exp. 5 | Exp. 6 | Mean | Evaluation |
|---|---|---|---|---|---|---|---|---|
| CL-2 | 27 | 16 | 13 | 34 | 23 | | 23 | ○ |
| CL-1 | | | | 28 | | | 28 | ○ |
| CL-4 | | | | 6 | 15 | | 11 | ○ |
| CL-9 | 22 | 9 | 6 | | | | 12 | ○ |
| CL-10 | 18 | 11 | | | | | 15 | ○ |
| CL-3 | 38 | 16 | | | | | 27 | ○ |
| AS-2 | 73 | 66 | | | | | 70 | x |
| LL-5 | 8 | 24 | 4 | | | | 12 | ○ |
| AS-1 | 95 | 100 | 114 | | | | 103 | x |
| LL-1 | | | | | | 84 | 84 | x |
| LL-2 | | | | | | 44 | 44 | x |
| LL-3 | | | | | | 32 | 32 | x |
| LL-4 | | | | | | 41 | 41 | x |

As described above, it is evident that the circular TNNA-containing nucleic acid molecule dimer sufficiently produces knockdown effects.

Example 3: Knockdown Effects of Circular TNNA-Containing Nucleic Acid Molecule Dimer—(2)

Figure 5:
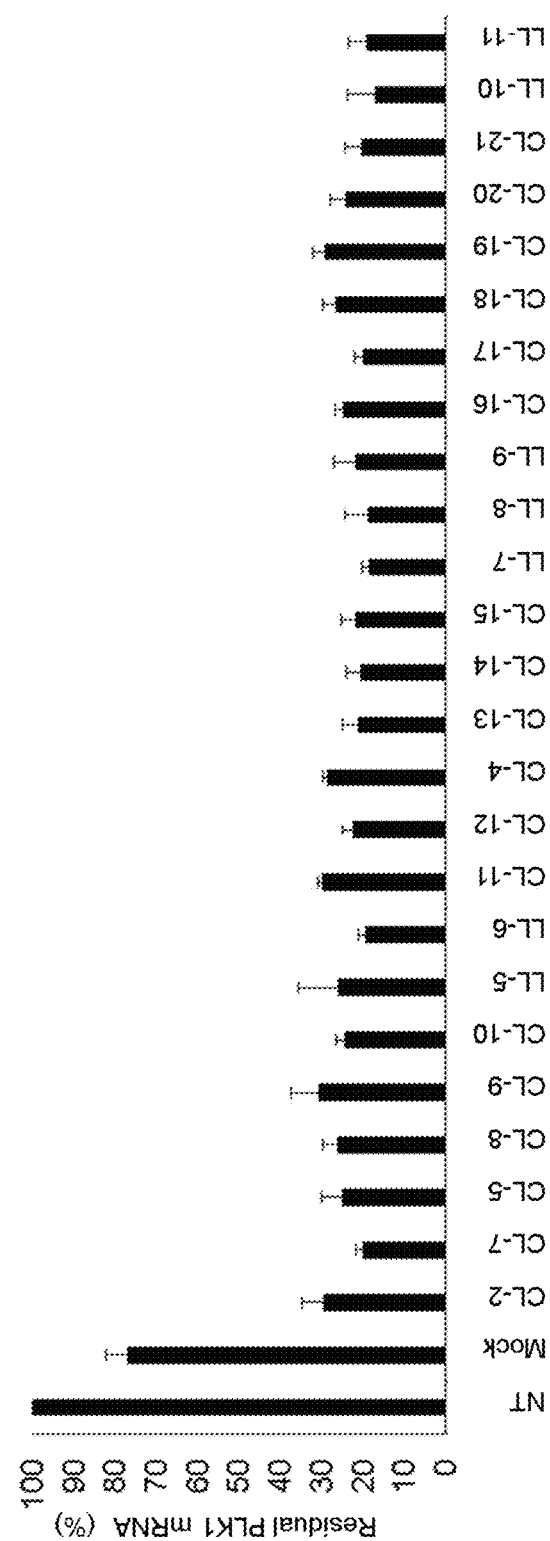
FIG. 5 is a graph showing results of evaluating the KD effects of various nucleic acid molecule dimers.

Circular TNNA-containing nucleic acid molecule dimers having various structures differing in the presence or absence of a overhang or a gap were studied for their knockdown effects. Briefly, the knockdown effects of each nucleic acid molecule dimer were evaluated on the basis of the residual rate of mRNA in the same way as in Example 2 except that: the A549 cells were inoculated at a density of 2×10³ cells/well to a 96-well plate; and the final concentration of each nucleic acid molecule dimer shown in FIG. 5 was set to 20 nM. From the results shown in FIG. 5, it is evident that the circular TNNA-containing nucleic acid molecule dimer exerts sufficient knockdown effects, irrespective of the presence or absence of a overhang or whether TCNA has a nick or has a gap.

Example 4: Knockdown Effects of Circular TNNA-Containing Nucleic Acid Molecule Dimer—(3)

Circular TNNA-containing nucleic acid molecule dimers having a modification to TCNA were studied for their knockdown effects. Briefly, the knockdown effects of each nucleic acid molecule dimer were evaluated in the same way as in Example 2 except that the nucleic acid molecule dimers described in Table 7 were used.

TABLE 7 mRNA residual rate of nucleic acid molecule dimers having a modification to TCNA

| Sample name | Mean % | SD |
|---|---|---|
| NT | 100 | 9.6 |
| CL-2 | 30 | 2.4 |
| CL-22 | 24 | 4.8 |
| CL-23 | 24 | 1.5 |
| LL-5 | 9 | 0.5 |
| LL-12 | 13 | 0.7 |
| LL-13 | 16 | 0.6 |

From the results shown in Table 7, it is evident that the circular TNNA-containing nucleic acid molecule dimer exerts sufficient knockdown effects even if TCNA is modified.

Example 5: Knockdown Effects of Circular TNNA-Containing Nucleic Acid Molecule Dimer—(4)

Circular TNNA-containing nucleic acid molecule dimers targeting another nucleic acid molecule were studied for their knockdown effects. Briefly, the knockdown effects of each nucleic acid molecule dimer were evaluated on the basis of the residual rate of mRNA in the same way as in Example 2 except that: the A549 cells were inoculated at a density of $2.5 \times 10^4$ cells/well to a 6-well plate; and the final concentration of each nucleic acid molecule dimer shown in Table 8 was set to 20 nM. The results are shown in Table 8. Numerical values are relative values when each measurement value was normalized with a GAPDH measurement value and the value of a mock control (Mock) supplemented with a transfection reagent alone was defined as 100.

TABLE 8 mRNA residual rate of nucleic acid molecule dimers targeting GFP

| Sample name | mRNA residual rate (Mock = 100) |
|---|---|
| CL-24 | 20 |
| LL-14 | 2 |
| LL-15 | 2 |
| CL-25 | 9 |
| LL-16 | 4 |
| LL-17 | 2 |

From the results shown in the table, it is evident that the circular TNNA-containing nucleic acid molecule dimer exerts sufficient knockdown effects on a different target nucleic acid molecule.

Example 6: Circumvention of Off-Target Effects by Circular TNNA-Containing Nucleic Acid Molecule Dimer The presence or absence of off-target effects ascribable to TNNA was evaluated by comparing the knockdown effects between a circular TNNA-containing nucleic acid molecule dimer and its corresponding circularized-TCNA nucleic acid molecule dimer. The residual rate of mRNA was measured in the same way as in Example 2 using CL-4 as the circular TNNA-containing nucleic acid molecule dimer and LC-1 as the circularized-TCNA nucleic acid molecule dimer. The results are shown in the table below. The residual rate of mRNA was indicated in the same way as in Example 2. A mRNA residual rate of 40% or less at a concentration of 1 nM was determined as pass (represented by circle).

TABLE 9

Off-target effects of circular TNNA-containing nucleic acid molecule dimers

| Name | mRNA residual rate (%, NT = 100%) (1 nM) | Evaluation |
|---|---|---|
| CL-4 | 40 | ○ |
| LC-1 | 98 | x |

From the results described above, it is evident that the residual rate of mRNA was not decreased by circularizing the nucleic acid molecule inducing RNA silencing (TCNA) and linearizing TNNA, whereas the residual rate of mRNA was decreased by linearizing TCNA and circularizing TNNA. This suggests that the off-target effects derived from TNNA can be suppressed by the circularization of TNNA (TCNA is linear).

Example 7: Circumvention of PKR Phosphorylation by Circular TNNA-Containing Nucleic Acid Molecule Dimer Circular TNNA-containing nucleic acid molecule dimers were evaluated for whether to be able to circumvent the activation (phosphorylation) of PKR. A549 cells were inoculated at a density of 0.25×10$^5$ cells/well to a 6-well plate and incubated at 37° C. under 5% $CO_2$ in DMEM medium containing 10% FBS. On the next day, a sample containing Lipofectamine RNAiMAX Transfection Reagent (Thermo Fisher Scientific Inc.) and each nucleic acid molecule dimer in Opti-MEM (Sigma-Aldrich Co. LLC) medium was added to the A549 cell cultures according to manufacturer's protocol such that the final concentration of the nucleic acid molecule dimer was 20 nM, followed by transfection for 5 hours. After the transfection, the medium was replaced with DMEM medium containing 10% FBS. 24 hours after the start of the transfection, the residual rate of PLK1 mRNA was measured in the same way as in Example 2 using an aliquot of the cultures.

Figure 6:
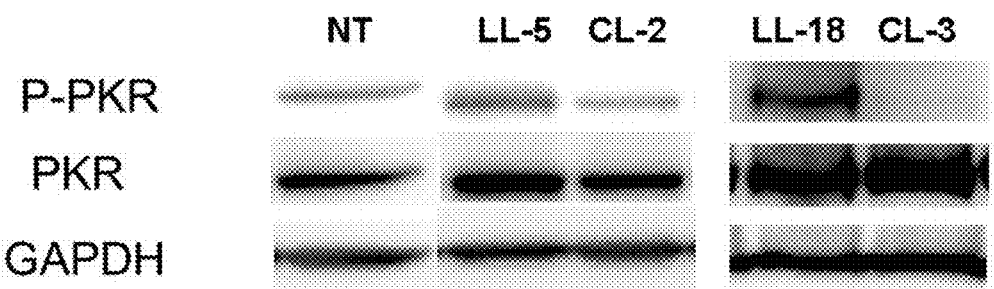
FIG. 6 is a diagram showing results of evaluating by Western blotting the degree of phosphorylation of PKR in cells on which a circular TNNA-containing nucleic acid molecule dimer or its corresponding linear nucleic acid molecule dimer was allowed to act. P-PKR represents phosphorylated PKR.

72 hours after the start of the transfection, the cultures were lysed in a lysis buffer to extract proteins, which were then subjected to Western blotting in order to detect phosphorylated PKR. The composition of the lysis buffer involved 100 µL of 1% NP-40 (NP-40 Alternative PROTEIN GRADE Detergent, 10% Solution, Sterile—Filtered, Calbiochem), 500 µL of 1 M Tris-HCl (pH 7.5), 300 µL of 5 M NaCl, 20 µL of 0.5 M EDTA (pH 8.0), 9.08 mL of dialyzed water, one tablet of Complete, Mini, EDTA-free (F. Hoffmann-La Roche, Ltd.), and one tablet of PhosSTOP (F. Hoffmann-La Roche, Ltd.) in a total of 10 ml. The blot membrane was blocked with 5% PhosphoBLOCKER Blocking Reagent (Cell Biolabs, Inc., AKR-103) and reacted with a primary antibody (anti-P-PKR antibody (ab32036, diluted 1/1000), anti-PKR antibody (ab32052, diluted 1/1000) and anti-GAPDH antibody (ab8245, diluted 1/5000)) and subsequently with a secondary antibody (ECL anti-rabbit IgG antibody, diluted 1/4000), and a band was detected using Amersham ECL Prime Western blotting detection reagent (GE Healthcare Japan Corp., RPN2232). The results about the residual rate of mRNA are shown in Table 10, and the results of Western blotting are shown in FIG. 6. In the table, the residual rate of mRNA was indicated by ratio (%) when the residual rate of mRNA in an untreated group (NT) was defined as 100%. A mRNA residual rate KD efficiency of 25% or less at a RNA concentration of 20 nM was determined as pass (represented by circle).

TABLE 10 mRNA residual rate of circular TNNA-containing nucleic acid molecule dimers

| Name | mRNA residual rate (%, NT = 100%) (1 nM) | Evaluation |
| --- | --- | --- |
| CL-2 | 22.9 | ○ |
| CL-3 | 17.2 | ○ |

TABLE 10-continued mRNA residual rate of circular TNNA-containing nucleic acid molecule dimers

| Name | mRNA residual rate (%, NT = 100%) (1 nM) | Evaluation |
| --- | --- | --- |
| LL-5 | 5.5 | ○ |
| LL-18 | 3.8 | ○ |

From the results shown in FIG. 6, it is evident that the degree of phosphorylation of PKR in cells on which the circular TNNA-containing nucleic acid molecule dimer was allowed to act was markedly small as compared with the corresponding linear nucleic acid molecule dimer.

Figure 7:
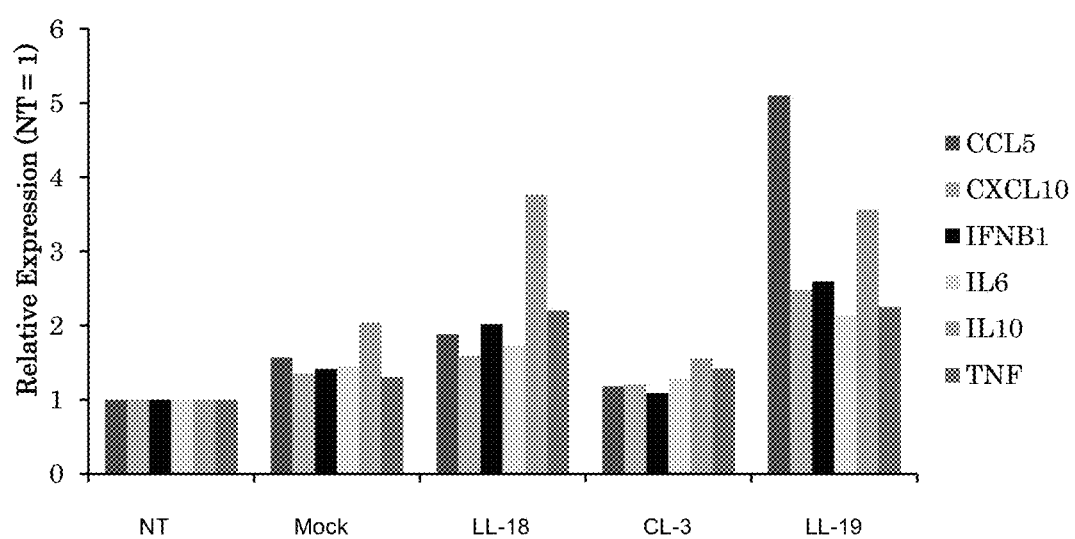
FIG. 7 is a graph showing the expression levels of TLR3 pathway-related genes in cells on which each of various nucleic acid molecules was allowed to act.

Example 8: Circumvention of TLR3 Pathway Activation by Circular TNNA-Containing Nucleic Acid Molecule Dimer A circular TNNA-containing nucleic acid molecule dimer was evaluated by various approaches for whether to be able to circumvent the activation (induction of expression of related genes) of the TLR3 pathway.
(1) Evaluation by Quantitative PCR A549 cells were inoculated at a density of 0.25×10$^5$ cells/well to a 6-well plate and incubated at 37° C. under 5% $CO_2$ in DMEM medium containing 10% FBS. On the next day, a sample containing Lipofectamine RNAiMAX Transfection Reagent (Thermo Fisher Scientific Inc.) and each nucleic acid molecule in Opti-MEM (Sigma-Aldrich Co. LLC) medium was added to the A549 cell cultures according to manufacturer's protocol such that the final concentration of the nucleic acid molecule dimer was 20 nM, followed by transfection for 6 hours. After the transfection, the medium was replaced with DMEM medium containing 10% FBS. 24 hours after the start of the transfection, the expression levels of CCL5, CXCL10, IFNα1, IFNβ1, IL6, IL10 and TNF related to the TLR3 pathway were measured in the same way as in Example 2 using an aliquot of the cultures. An untreated control (NT) and a mock control (Mock) supplemented with a transfection reagent alone were used as controls. From the results shown in FIG. 7, it is evident that the circular TNNA-containing nucleic acid molecule dimer causes less induction of expression of the TLR3 pathway-related genes as compared with classic siRNA or an asymmetric linear nucleic acid molecule dimer.
(2) Evaluation Using PCR Array A549 cells were inoculated at a density of 0.25×10$^5$ cells/well to a 6-well plate and incubated at 37° C. under 5% $CO_2$ in DMEM medium containing 10% FBS. On the next day, a sample containing Lipofectamine RNAiMAX Transfection Reagent (Thermo Fisher Scientific Inc.) and each nucleic acid molecule in Opti-MEM (Sigma-Aldrich Co. LLC) medium was added to the A549 cell cultures according to manufacturer's protocol such that the final concentration of the nucleic acid molecule dimer was 20 nM, followed by transfection for 5 hours. After the transfection, the medium was replaced with DMEM medium containing 10% FBS. 24 hours after the start of the transfection, RNA was extracted using RNeasy Mini Kit (Qiagen N.V.) and subjected to reverse transcription reaction using RT$^2$ First strand kit (Qiagen N.V.). Then, real-time PCR was performed using RT$^2$ Profiler PCR array (Qiagen N.V.) to measure the mRNA expression levels of the genes related to the TLR3 pathway. The table below shows results about genes whose expression level differed by two or more times between NT and each nucleic acid molecule. Numerical values are ratios to values in an untreated control (NT) defined as 1 by correcting means with housekeeping genes (ACTB/B2M/GAPDH/HPRT1).

TABLE 11 mRNA expression levels of genes related to TLR3 pathway

| | Fold change (NT = 1) | | |
|---|---|---|---|
| Gene | LL-18 | CL-3 | LL-20 |
| CCL5 | 2.3288 | 0.945 | 2.0533 |
| CXCR4 | 5.7134 | 1.5762 | 2.8988 |
| IL13 | 2.4921 | 0.5858 | 1.8599 |
| IL1B | 4.5509 | 1.8478 | 4.0822 |
| SOCS1 | 7.7155 | 1.71 | 9.8788 |

From the results shown in this table, it is evident that the expression of genes (CCL2, CCL5, and IL1B) expressed downstream of the TLR3 pathway was not induced in cells on which the circular TNNA-containing nucleic acid molecule dimer was allowed to act, as compared with classic siRNA or an asymmetric linear nucleic acid molecule dimer.

(3) Evaluation by Western Blotting

Figure 8:
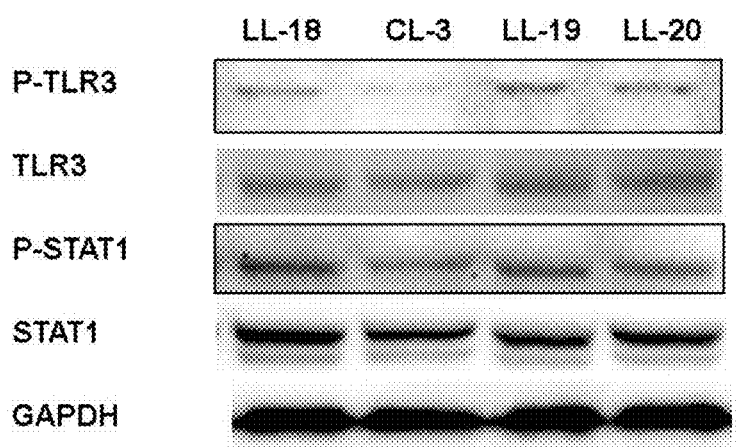
FIG. 8 is a diagram showing the phosphorylation of proteins (TLR3 and STAT1) related to the TLR3 pathway in cells on which each of various nucleic acid molecules was allowed to act.

A549 cells were inoculated at a density of 0.25×10$^5$ cells/well to a 6-well plate and incubated at 37° C. under 5% $CO_2$ in DMEM medium containing 10% FBS. On the next day, a sample containing Lipofectamine RNAiMAX Transfection Reagent (Thermo Fisher Scientific Inc.) and each nucleic acid molecule dimer in Opti-MEM (Sigma-Aldrich Co. LLC) medium was added to the A549 cell cultures according to manufacturer's protocol such that the final concentration of the nucleic acid molecule dimer was 20 nM, followed by transfection for 6 hours. 6 hours after the start of the transfection, the cultures were lysed in a lysis buffer in the same way as in Example 7 to extract proteins, which were then subjected to Western blotting in order to detect phosphorylated proteins related to the TLR3 pathway. The blot membrane was blocked with 5% PhosphoBLOCKER Blocking Reagent (Cell Biolabs, Inc., AKR-103) and reacted with a primary antibody (anti-P-TLR3 antibody (NBP2-24904, diluted 1/1000), anti-TLR3 antibody (ab62566, diluted 1/1000), GAPDH (ab8245, diluted 1/5000), anti-P-STAT1 antibody (SC-8394, diluted 1/200), anti-STAT-1 antibody (SC-464, diluted 1/200)) and subsequently with a secondary antibody (ECL anti-rabbit IgG antibody, diluted 1/4000, and ECL anti-mouse IgG antibody, diluted 1/2000), and a band was detected using Amersham ECL Prime Western blotting detection reagent (GE Healthcare Japan Corp., RPN2232). From the results shown in FIG. 8, it is evident that the TLR3 pathway was not activated because the phosphorylation of proteins (TLR3 and STAT1) related to the TLR3 pathway was not induced in cells on which the circular TNNA-containing nucleic acid molecule dimer was allowed to act, as compared with classic siRNA or an asymmetric linear nucleic acid molecule dimer.

Example 9: Evaluation of Exonuclease Resistance

Figure 9:
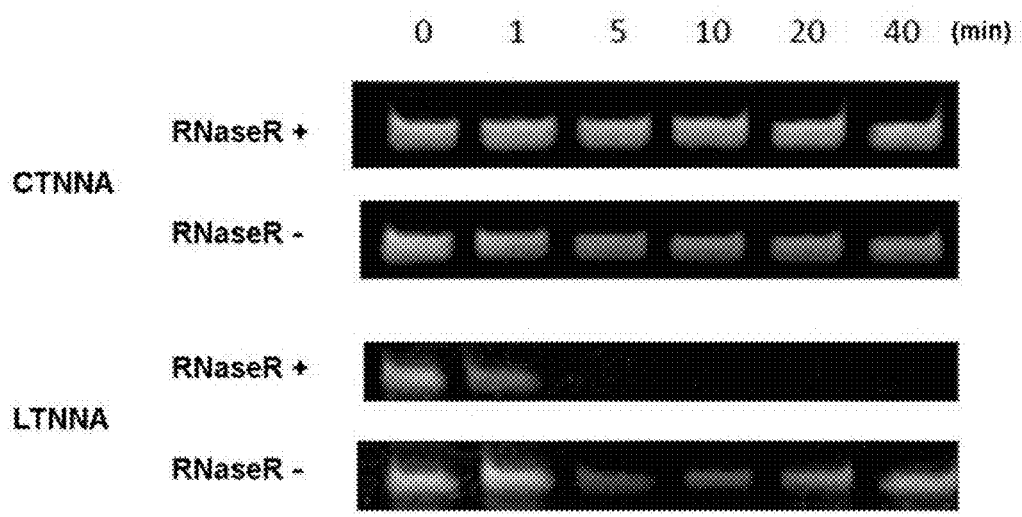
FIG. 9 is a graph showing results of evaluating the exonuclease resistance of CTNNA and LTNNA.

A circularized nucleic acid molecule was evaluated for its stability against exonuclease. Circular or linear TNNA was added at 20 µM to an exonuclease solution (RNase R, Epicentre Technologies Corp., 4.5 U) to adjust the whole amount to 100 µL. The sample was incubated at 37° C. After a lapse of 0, 5, 10, 20 and 40 minutes, an aliquot of the sample was recovered and preserved at −80° C. Each of all the samples thus recovered was applied to 20% denaturing polyacrylamide gel and electrophoresed at 200 V for 70 minutes. The gel was stained with 0.5 µg/mL ethidium bromide for 15 minutes, and the amount of a band was evaluated with UV. From the results shown in FIG. 9, it is evident that the circular nucleic acid molecule has markedly high resistance to exonuclease as compared with the linear nucleic acid molecule.

Example 10: Knockdown Effects of Circular TNNA-Containing Nucleic Acid Molecule Dimer—(5)

A circularized-TNNA nucleic acid molecule dimer targeting another nucleic acid molecule was studied for its knockdown effects. Nucleic acid molecule dimers targeting MT1MMP as shown in Tables 12 and 13 were used. Each nucleic acid molecule dimer was prepared in the same way as in Example 1.

TABLE 12

Sequences of TNNA and TCNA

| | Name | Sequence | SEQ ID NO |
|---|---|---|---|
| Seq. of TNNA | TN-01 | 5'-P-CCAAUGUUGAUCAA GG-3' | 36 |
| | TN-02 | 5'-UGAGAUCAAGGCCAAU GUUdTdT-3' | 37 |
| Seq. of TCNA | TC-01 | 5'-AACAUUGGCCUUGAUC UCA-3' | 38 |
| | TC-02 | 5'-AACAUUGGCCUUGAUC UCAdTdT-3' | 39 |

TABLE 13

Configuration of nucleic acid molecule dimers

| Name | TNNA | TCNA | Length (TN/TC) | Structure |
|---|---|---|---|---|
| CL-01 | TN-01 | TC-01 | 16/19 | Circular, 3' end overhang on TCNA |
| LL-01 | TN-02 | TC-02 | 21/21 | Linear, 3' end overhang on TNNA and TCNA |

The MT1MMP knockdown effects of the nucleic acid molecule dimers were evaluated in the same way as in Example 2 except that: MDA-MB231 was used as cells; the nucleic acid molecule dimers shown in Tables 12 and 13 were used; and the expression level of MT1MMP was to be measured. The results are shown in Table 14. In the table, the residual rate of mRNA was indicated by ratio (%) when the residual rate of mRNA in an untreated group (NT) was defined as 100%. A mRNA residual rate of 30% or less at a RNA concentration of 10 nM was determined as pass (represented by circle).

TABLE 14 mRNA residual rate of various nucleic acid molecule dimers

| Sample name | mRNA residual rate (%, NT = 100%) | Evaluation |
|---|---|---|
| CL-01 | 25.7 | ○ |
| LL-01 | 9.0 | ○ |

As described above, it is evident that the knockdown effects of the circular TNNA-containing nucleic acid molecule dimer are not limited by a particular gene.

Example 11: Knockdown Effects of Circular TNNA-Containing Nucleic Acid Molecule Dimer Comprising Sequence of miRNA Circularized-TNNA nucleic acid molecule dimers comprising the nucleotide sequence of miRNA were studied for their knockdown effects. The sequence of hsa-miR-34a-5p was used as the nucleotide sequence of miRNA. Each nucleic acid molecule dimer was prepared in the same way as in Example 1. The sequences used are shown in Table 15, and the configuration of each nucleic acid molecule dimer is shown in Table 16.

TABLE 15

Sequences of TNNA and TCNA

| | Name | Sequence | SEQ ID NO |
|---|---|---|---|
| Seq. of TNNA | TN-03 | 5'-ACCAGCUAAGACACUGCCA-3' | 40 |
| | TN-04 | 5'-P-GACACUGCCAACCAGCUAA-3' | 41 |
| Seq. of TCNA | TC-03 | 5'-P-UGGCAGUGUCUUAGCUGGUUGU-3' | 42 |
| | TC-04 | 5'-UGGCAGUGUCUUAGCUGGUUGU-3' | 43 |

TABLE 16

Configuration of nucleic acid molecule dimers

| Name | TNNA | TCNA | Length (TN/TC) | Structure |
|---|---|---|---|---|
| LL-02 | TN-03 | TC-03 | 19/22 | Linear, 3' end overhang on TCNA |
| CL-02 | TN-04 | TC-03 | 19/22 | Circular, 3' end overhang on TCNA |
| CL-03 | TN-04 | TC-04 | 19/22 | Circular, 3' end overhang on TCNA |

Figure 10:
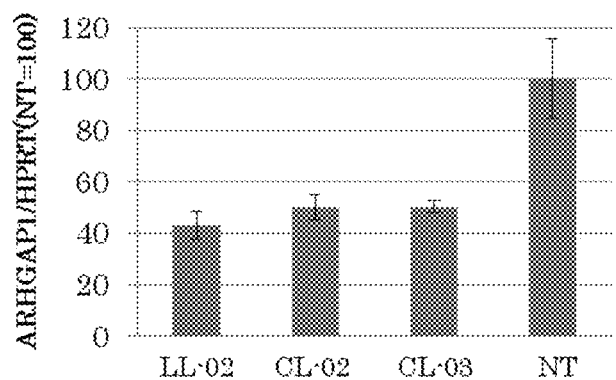
FIG. 10 is a graph showing results of evaluating the KD effects of various nucleic acid molecule dimers. The ordinate shows the expression rate of ARHGAP1 normalized with endogenous control HPRT.

The ARHGAP1 knockdown effects of the nucleic acid molecule dimers were evaluated in the same way as in Example 3 except that: HCT116 was used as cells; the nucleic acid molecule dimers shown in Tables 15 and 16 were used; and the expression level of ARHGAP1 was to be measured. ARHGAP1 is a target gene of miR-34a, and its expression is known to be suppressed by miR-34a (Matsui et al., Mol Ther. 2016; 24 (5): 946-55). As seen from the results shown in FIG. 10, all the circular TNNA-containing nucleic acid molecule dimers exhibited marked knockdown effects as compared with an untreated group (NT).

Those skilled in the art will understand that many various modifications can be made in the present invention without departing from the spirit of the present invention. Thus, it should be understood that the modes of the present invention described in the present specification are given merely for illustrative purposes and are not intended to limit the scope of the present invention.

What is claimed is:

1. A nucleic acid molecule dimer comprising:
   a first nucleic acid molecule of 15 to 30 mer having at least 80% complementarity to at least a portion of a target nucleic acid molecule; and
   a second nucleic acid molecule of 12 to 30 mer having at least 76% complementarity to the first nucleic acid molecule,
   wherein the first nucleic acid molecule is linear, the second nucleic acid molecule is circular, and the first nucleic acid molecule and the second nucleic acid molecule at least partially form a duplex.

2. The nucleic acid molecule dimer according to claim 1, wherein the first nucleic acid molecule is longer than the second nucleic acid molecule.

3. The nucleic acid molecule dimer according to claim 1, wherein the 3' end or the 5' end of the first nucleic acid molecule forms a overhang.

4. The nucleic acid molecule dimer according to claim 1, wherein the first nucleic acid molecule forms a nick.

5. The nucleic acid molecule dimer according to claim 1, wherein the length of the first nucleic acid molecule is 19 to 21 mer.

6. The nucleic acid molecule dimer according to claim 1, wherein the length of the second nucleic acid molecule is 16 to 25 mer.

7. The nucleic acid molecule dimer according to claim 1, wherein the first nucleic acid molecule and/or the second nucleic acid molecule is modified.

8. A composition comprising the nucleic acid molecule dimer according to claim 1.

9. A pharmaceutical composition comprising the nucleic acid molecule dimer according to claim 1 and one or more pharmaceutically acceptable additives.

10. A method for modulating the expression of a target nucleic acid molecule, comprising administering an effective amount of the nucleic acid molecule dimer according to claim 1 to a cell containing the target nucleic acid molecule.

11. The method according to claim 10, wherein the method is performed in vitro, ex vivo or in vivo.

12. The nucleic acid molecule dimer according to claim 1, wherein the first nucleic acid molecule has at least 85% complementarity to at least a portion of a target nucleic acid molecule.

13. The nucleic acid molecule dimer according to claim 1, wherein the first nucleic acid molecule has at least 90% complementarity to at least a portion of a target nucleic acid molecule.

14. The nucleic acid molecule dimer according to claim 1, wherein the second nucleic acid molecule has at least 80% complementarity to the first nucleic acid molecule.

15. The nucleic acid molecule dimer according to claim 1, wherein the first nucleic acid molecule has at least 90% complementarity to the first nucleic acid molecule.

16. The method according to claim 10, wherein the method is performed in vitro or ex vivo.

* * * * *

UNITED STATES PATENT AND TRADEMARK OFFICE
CERTIFICATE OF CORRECTION

PATENT NO. : 11,298,371 B2
APPLICATION NO. : 16/754595
DATED : April 12, 2022
INVENTOR(S) : Kenjiro Minomi et al.

It is certified that error appears in the above-identified patent and that said Letters Patent is hereby corrected as shown below:

On the Title Page

Column 1 (Item (87) PCT Pub. No.), Line 1, delete "WO2018" and insert -- WO2019 --.

In the Specification

Column 24, Line 8, delete "-dide-oxythymidine" and insert -- -dideoxythymidine --.

Signed and Sealed this
Eleventh Day of October, 2022

Katherine Kelly Vidal
Director of the United States Patent and Trademark Office

SEQUENCE LISTING

```
<160> NUMBER OF SEQ ID NOS: 43

<210> SEQ ID NO 1
<211> LENGTH: 16
<212> TYPE: RNA
<213> ORGANISM: Artificial sequence
<220> FEATURE:
<223> OTHER INFORMATION: TN-1
<220> FEATURE:
<221> NAME/KEY: misc_feature
<222> LOCATION: (1)..(1)
<223> OTHER INFORMATION: phosphate group at 5' end

<400> SEQUENCE: 1
gagcugcucc auuaac                                                       16

<210> SEQ ID NO 2
<211> LENGTH: 16
<212> TYPE: RNA
<213> ORGANISM: Artificial sequence
<220> FEATURE:
<223> OTHER INFORMATION: TN-2
<220> FEATURE:
<221> NAME/KEY: misc_feature
<222> LOCATION: (1)..(1)
<223> OTHER INFORMATION: phosphate group at 5' end

<400> SEQUENCE: 2
cugcuuaauu aacgag                                                       16

<210> SEQ ID NO 3
<211> LENGTH: 16
```

```
<212> TYPE: RNA
<213> ORGANISM: Artificial sequence
<220> FEATURE:
<223> OTHER INFORMATION: TN-3
<220> FEATURE:
<221> NAME/KEY: misc_feature
<222> LOCATION: (1)..(1)
<223> OTHER INFORMATION: phosphate group at 5' end

<400> SEQUENCE: 3
gaauaugacc aaaguc                                                      16

<210> SEQ ID NO 4
<211> LENGTH: 18
<212> TYPE: RNA
<213> ORGANISM: Artificial sequence
<220> FEATURE:
<223> OTHER INFORMATION: TN-4
<220> FEATURE:
<221> NAME/KEY: misc_feature
<222> LOCATION: (1)..(1)
<223> OTHER INFORMATION: phosphate group at 5' end

<400> SEQUENCE: 4
cugcuuaaca uuaacgag                                                    18

<210> SEQ ID NO 5
<211> LENGTH: 19
<212> TYPE: RNA
<213> ORGANISM: Artificial sequence
<220> FEATURE:
<223> OTHER INFORMATION: TN-5
<220> FEATURE:
<221> NAME/KEY: misc_feature
<222> LOCATION: (1)..(1)
<223> OTHER INFORMATION: phosphate group at 5' end

<400> SEQUENCE: 5
cugcuuaacc auuaacgag                                                   19

<210> SEQ ID NO 6
<211> LENGTH: 19
<212> TYPE: RNA
<213> ORGANISM: Artificial sequence
<220> FEATURE:
<223> OTHER INFORMATION: TN-6
<220> FEATURE:
<221> NAME/KEY: misc_feature
<222> LOCATION: (1)..(1)
<223> OTHER INFORMATION: phosphate group at 5' end

<400> SEQUENCE: 6
gaauaugaca accaaaguc                                                   19

<210> SEQ ID NO 7
<211> LENGTH: 21
<212> TYPE: RNA
<213> ORGANISM: Artificial sequence
<220> FEATURE:
<223> OTHER INFORMATION: TN-7
<220> FEATURE:
<221> NAME/KEY: misc_feature
<222> LOCATION: (1)..(1)
<223> OTHER INFORMATION: phosphate group at 5' end

<400> SEQUENCE: 7
cugcuuaaaa ccauuaacga g                                                21

<210> SEQ ID NO 8
```

```
<211> LENGTH: 23
<212> TYPE: RNA
<213> ORGANISM: Artificial sequence
<220> FEATURE:
<223> OTHER INFORMATION: TN-8
<220> FEATURE:
<221> NAME/KEY: misc_feature
<222> LOCATION: (1)..(1)
<223> OTHER INFORMATION: phosphate group at 5' end

<400> SEQUENCE: 8
cugcuuaacc aaccauuaac gag                                    23

<210> SEQ ID NO 9
<211> LENGTH: 25
<212> TYPE: RNA
<213> ORGANISM: Artificial sequence
<220> FEATURE:
<223> OTHER INFORMATION: TN-9
<220> FEATURE:
<221> NAME/KEY: misc_feature
<222> LOCATION: (1)..(1)
<223> OTHER INFORMATION: phosphate group at 5' end

<400> SEQUENCE: 9
cugcuuaagc ccaaccauua acgag                                  25

<210> SEQ ID NO 10
<211> LENGTH: 16
<212> TYPE: RNA
<213> ORGANISM: Artificial sequence
<220> FEATURE:
<223> OTHER INFORMATION: TN-10
<220> FEATURE:
<221> NAME/KEY: misc_feature
<222> LOCATION: (1)..(1)
<223> OTHER INFORMATION: phosphate group at 5' end

<400> SEQUENCE: 10
uucaaggacc aucuuc                                            16

<210> SEQ ID NO 11
<211> LENGTH: 16
<212> TYPE: RNA
<213> ORGANISM: Artificial sequence
<220> FEATURE:
<223> OTHER INFORMATION: TN-11
<220> FEATURE:
<221> NAME/KEY: misc_feature
<222> LOCATION: (1)..(1)
<223> OTHER INFORMATION: phosphate group at 5' end

<400> SEQUENCE: 11
ucuucuucgc gcacca                                            16

<210> SEQ ID NO 12
<211> LENGTH: 16
<212> TYPE: RNA
<213> ORGANISM: Artificial sequence
<220> FEATURE:
<223> OTHER INFORMATION: TN-12

<400> SEQUENCE: 12
ccauuaacga gcugcu                                            16

<210> SEQ ID NO 13
<211> LENGTH: 16
<212> TYPE: RNA
<213> ORGANISM: Artificial sequence
```

```
<220> FEATURE:
<223> OTHER INFORMATION: TN-13

<400> SEQUENCE: 13
cugcuuaauu aacgag                                                    16

<210> SEQ ID NO 14
<211> LENGTH: 16
<212> TYPE: RNA
<213> ORGANISM: Artificial sequence
<220> FEATURE:
<223> OTHER INFORMATION: TN-14

<400> SEQUENCE: 14
uuaacgagcu gcuuaa                                                    16

<210> SEQ ID NO 15
<211> LENGTH: 16
<212> TYPE: RNA
<213> ORGANISM: Artificial sequence
<220> FEATURE:
<223> OTHER INFORMATION: TN-15

<400> SEQUENCE: 15
ccaaagucga auauga                                                    16

<210> SEQ ID NO 16
<211> LENGTH: 19
<212> TYPE: RNA
<213> ORGANISM: Artificial sequence
<220> FEATURE:
<223> OTHER INFORMATION: TN-16

<400> SEQUENCE: 16
ccauuaacga gcugcuuaa                                                 19

<210> SEQ ID NO 17
<211> LENGTH: 19
<212> TYPE: RNA
<213> ORGANISM: Artificial sequence
<220> FEATURE:
<223> OTHER INFORMATION: TN-17

<400> SEQUENCE: 17
cugcuuaacc auuaacgag                                                 19

<210> SEQ ID NO 18
<211> LENGTH: 19
<212> TYPE: RNA
<213> ORGANISM: Artificial sequence
<220> FEATURE:
<223> OTHER INFORMATION: TN-18

<400> SEQUENCE: 18
caaccaaagu cgaauauga                                                 19

<210> SEQ ID NO 19
<211> LENGTH: 21
<212> TYPE: DNA
<213> ORGANISM: Artificial sequence
<220> FEATURE:
<223> OTHER INFORMATION: TN-19
<220> FEATURE:
<221> NAME/KEY: misc_feature
<223> OTHER INFORMATION: Combined DNA/RNA molecule

<400> SEQUENCE: 19
```
ccauuaacga gcugcuuaat t                                                    21

<210> SEQ ID NO 20
<211> LENGTH: 21
<212> TYPE: DNA
<213> ORGANISM: Artificial sequence
<220> FEATURE:
<223> OTHER INFORMATION: TN-20
<220> FEATURE:
<221> NAME/KEY: misc_feature
<223> OTHER INFORMATION: Combined DNA/RNA molecule

<400> SEQUENCE: 20
caaccaaagu cgaauaugat t                                                    21

<210> SEQ ID NO 21
<211> LENGTH: 16
<212> TYPE: RNA
<213> ORGANISM: Artificial sequence
<220> FEATURE:
<223> OTHER INFORMATION: NT-21

<400> SEQUENCE: 21
ccaucuucuu caagga                                                          16

<210> SEQ ID NO 22
<211> LENGTH: 16
<212> TYPE: RNA
<213> ORGANISM: Artificial sequence
<220> FEATURE:
<223> OTHER INFORMATION: NT-22

<400> SEQUENCE: 22
gcgcaccauc uucuuc                                                          16

<210> SEQ ID NO 23
<211> LENGTH: 19
<212> TYPE: RNA
<213> ORGANISM: Artificial sequence
<220> FEATURE:
<223> OTHER INFORMATION: NT-23

<400> SEQUENCE: 23
gcaccaucuu cuucaagga                                                       19

<210> SEQ ID NO 24
<211> LENGTH: 19
<212> TYPE: RNA
<213> ORGANISM: Artificial sequence
<220> FEATURE:
<223> OTHER INFORMATION: TN-24

<400> SEQUENCE: 24
ggagcgcacc aucuucuuc                                                       19

<210> SEQ ID NO 25
<211> LENGTH: 19
<212> TYPE: RNA
<213> ORGANISM: Artificial sequence
<220> FEATURE:
<223> OTHER INFORMATION: TC-1

<400> SEQUENCE: 25
uuaagcagcu cguuaaugg                                                       19

```
<210> SEQ ID NO 26
<211> LENGTH: 19
<212> TYPE: RNA
<213> ORGANISM: Artificial sequence
<220> FEATURE:
<223> OTHER INFORMATION: TC-2

<400> SEQUENCE: 26
ucauauucga cuuugguug                                                    19

<210> SEQ ID NO 27
<211> LENGTH: 21
<212> TYPE: RNA
<213> ORGANISM: Artificial sequence
<220> FEATURE:
<223> OTHER INFORMATION: TC-3

<400> SEQUENCE: 27
uuaagcagcu cguuaauggu u                                                 21

<210> SEQ ID NO 28
<211> LENGTH: 21
<212> TYPE: DNA
<213> ORGANISM: Artificial sequence
<220> FEATURE:
<223> OTHER INFORMATION: TC-4
<220> FEATURE:
<221> NAME/KEY: misc_feature
<223> OTHER INFORMATION: Combined DNA/RNA

<400> SEQUENCE: 28
uuaagcagcu cguuaauggt t                                                 21

<210> SEQ ID NO 29
<211> LENGTH: 21
<212> TYPE: DNA
<213> ORGANISM: Artificial sequence
<220> FEATURE:
<223> OTHER INFORMATION: TC-5
<220> FEATURE:
<221> NAME/KEY: misc_feature
<223> OTHER INFORMATION: Combined DNA/RNA

<400> SEQUENCE: 29
ucauauucga cuuugguugt t                                                 21

<210> SEQ ID NO 30
<211> LENGTH: 19
<212> TYPE: RNA
<213> ORGANISM: Artificial sequence
<220> FEATURE:
<223> OTHER INFORMATION: TC-6
<220> FEATURE:
<221> NAME/KEY: misc_feature
<222> LOCATION: (7)..(7)
<223> OTHER INFORMATION: locked nucleic acid

<400> SEQUENCE: 30
uuaagcagcu cguuaaugg                                                    19

<210> SEQ ID NO 31
<211> LENGTH: 19
<212> TYPE: RNA
<213> ORGANISM: Artificial sequence
<220> FEATURE:
<223> OTHER INFORMATION: TC-7
<220> FEATURE:
<221> NAME/KEY: misc_feature
<222> LOCATION: (7)..(7)
```

```
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 31
uuaagcagcu cguuaaugg                                               19

<210> SEQ ID NO 32
<211> LENGTH: 19
<212> TYPE: RNA
<213> ORGANISM: Artificial sequence
<220> FEATURE:
<223> OTHER INFORMATION: TC-8
<220> FEATURE:
<221> NAME/KEY: misc_feature
<222> LOCATION: (1)..(1)
<223> OTHER INFORMATION: phosphate group at 5' end

<400> SEQUENCE: 32
uuaagcagcu cguuaaugg                                               19

<210> SEQ ID NO 33
<211> LENGTH: 19
<212> TYPE: RNA
<213> ORGANISM: Artificial sequence
<220> FEATURE:
<223> OTHER INFORMATION: TC-9

<400> SEQUENCE: 33
uccuugaaga agauggugc                                               19

<210> SEQ ID NO 34
<211> LENGTH: 19
<212> TYPE: RNA
<213> ORGANISM: Artificial sequence
<220> FEATURE:
<223> OTHER INFORMATION: TC-10

<400> SEQUENCE: 34
gaagaagaug gugcgcucc                                               19

<210> SEQ ID NO 35
<211> LENGTH: 16
<212> TYPE: RNA
<213> ORGANISM: Artificial sequence
<220> FEATURE:
<223> OTHER INFORMATION: TC-11

<400> SEQUENCE: 35
uuaagcagcu cguuaa                                                  16

<210> SEQ ID NO 36
<211> LENGTH: 16
<212> TYPE: RNA
<213> ORGANISM: Artificial Sequence
<220> FEATURE:
<223> OTHER INFORMATION: TN-01
<220> FEATURE:
<221> NAME/KEY: misc_feature
<222> LOCATION: (1)..(1)
<223> OTHER INFORMATION: phosphate group at 5' end

<400> SEQUENCE: 36
ccaauguuga ucaagg                                                  16
```

```
<210> SEQ ID NO 37
<211> LENGTH: 21
<212> TYPE: DNA
<213> ORGANISM: Artificial Sequence
<220> FEATURE:
<223> OTHER INFORMATION: TN-02
<220> FEATURE:
<221> NAME/KEY: misc_feature
<223> OTHER INFORMATION: Combined DNA/RNA molecule

<400> SEQUENCE: 37
ugagaucaag gccaauguut t                                              21

<210> SEQ ID NO 38
<211> LENGTH: 19
<212> TYPE: RNA
<213> ORGANISM: Artificial Sequence
<220> FEATURE:
<223> OTHER INFORMATION: TC-01

<400> SEQUENCE: 38
aacauuggcc uugaucuca                                                 19

<210> SEQ ID NO 39
<211> LENGTH: 21
<212> TYPE: DNA
<213> ORGANISM: Artificial Sequence
<220> FEATURE:
<223> OTHER INFORMATION: TC-02
<220> FEATURE:
<221> NAME/KEY: misc_feature
<223> OTHER INFORMATION: Combined DNA/RNA molecule

<400> SEQUENCE: 39
aacauuggcc uugaucucat t                                              21

<210> SEQ ID NO 40
<211> LENGTH: 19
<212> TYPE: RNA
<213> ORGANISM: Artificial Sequence
<220> FEATURE:
<223> OTHER INFORMATION: TN-03

<400> SEQUENCE: 40
accagcuaag acacugcca                                                 19

<210> SEQ ID NO 41
<211> LENGTH: 19
<212> TYPE: RNA
<213> ORGANISM: Artificial Sequence
<220> FEATURE:
<223> OTHER INFORMATION: TN-04
<220> FEATURE:
<221> NAME/KEY: misc_feature
<222> LOCATION: (1)..(1)
<223> OTHER INFORMATION: phosphate group at 5' end

<400> SEQUENCE: 41
gacacugcca accagcuaa                                                 19

<210> SEQ ID NO 42
<211> LENGTH: 22
<212> TYPE: RNA
<213> ORGANISM: Artificial Sequence
<220> FEATURE:
<223> OTHER INFORMATION: TC-03
<220> FEATURE:
<221> NAME/KEY: misc_feature
<222> LOCATION: (1)..(1)
```

```
<223> OTHER INFORMATION: phosphate group at 5' end

<400> SEQUENCE: 42
uggcaguguc uuagcugguu gu                                              22

<210> SEQ ID NO 43
<211> LENGTH: 22
<212> TYPE: RNA
<213> ORGANISM: Artificial Sequence
<220> FEATURE:
<223> OTHER INFORMATION: TC-04

<400> SEQUENCE: 43
uggcaguguc uuagcugguu gu                                              22
```